(12) United States Patent
Chen et al.

(10) Patent No.: US 11,795,152 B2
(45) Date of Patent: Oct. 24, 2023

(54) CRYSTAL FORM OF TAFAMIDIS AND PREPARATION METHOD THEREFOR AND USE THEREOF

(71) Applicant: CRYSTAL PHARMACEUTICAL (SUZHOU) CO., LTD., Jiangsu (CN)

(72) Inventors: Minhua Chen, Suzhou (CN); Jing Zhang, Jiangsu (CN); Siming Zou, Suzhou (CN)

(73) Assignee: CRYSTAL PHARMACEUTICAL (SUZHOU) CO., LTD., Suzhou (CN)

( * ) Notice: Subject to any disclaimer, the term of this patent is extended or adjusted under 35 U.S.C. 154(b) by 235 days.

(21) Appl. No.: 17/392,008

(22) Filed: Aug. 2, 2021

(65) Prior Publication Data

US 2021/0363116 A1    Nov. 25, 2021

Related U.S. Application Data

(63) Continuation of application No. PCT/CN2020/128376, filed on Nov. 12, 2020.

(30) Foreign Application Priority Data

Nov. 15, 2019 (CN) .......................... 201911118522.0
Nov. 26, 2019 (CN) .......................... 201911175626.5
Dec. 10, 2019 (CN) .......................... 201911256434.7

(51) Int. Cl.
C07D 263/57    (2006.01)

(52) U.S. Cl.
CPC ........ C07D 263/57 (2013.01); *C07B 2200/13* (2013.01)

(58) Field of Classification Search
CPC .................................................. C07D 263/57
See application file for complete search history.

(56) References Cited

U.S. PATENT DOCUMENTS 10,577,334 B2    3/2020    Chen et al.

FOREIGN PATENT DOCUMENTS

| CN | 103781770 A | 5/2014 |
| CN | 107344927 A | 11/2014 |
| CN | 106715405 A | 5/2017 |
| WO | 2004056315 A2 | 7/2004 |
| WO | 2013038351 A1 | 3/2013 |
| WO | 2016038500 A1 | 3/2016 |
| WO | 2019175263 A1 | 9/2019 |
| WO | 2020232325 A1 | 11/2020 |
| WO | 2021001858 A1 | 1/2021 |

OTHER PUBLICATIONS

International Application No. PCT/CN2020/128376, International Search Report and Written Opinion dated Feb. 18, 2021, 15 pages.

*Primary Examiner* — Shawquia Jackson
(74) *Attorney, Agent, or Firm* — MagStone Law, LLP; Enshan Hong

(57) ABSTRACT

The present disclosure relates to novel crystalline forms of tafamidis (hereinafter referred to as compound I) and processes for preparation thereof. The present disclosure also relates to pharmaceutical composition containing the novel crystalline forms, use of the novel crystalline forms for preparing drugs treating disease caused by transthyretin-mediated amyloidosis. The crystalline forms of tafamidis of the present disclosure have one or more improved properties compared with crystalline forms of prior art and have significant value for future drug optimization and development.

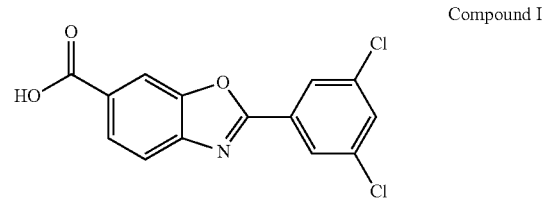

Compound I

19 Claims, 15 Drawing Sheets

CRYSTAL FORM OF TAFAMIDIS AND PREPARATION METHOD THEREFOR AND USE THEREOF

RELATED APPLICATIONS

This is a continuation application of PCT/CN2020/128376 filed on Nov. 12, 2020, which claims priority to China Patent Application Nos. 201911118522.0, 201911175626.5, and 201911256434.7 respectively filed on Nov. 15, 2019, Nov. 26, 2019, and Dec. 10, 2019 with China National Intellectual Property Administration (CNIPA), all of which are incorporated herein by reference in their entirety.

BACKGROUND OF THE INVENTION

1. Technical Field

The present disclosure relates to the field of chemical crystallography, particularly relates to novel crystalline forms of tafamidis, processes for preparation and use thereof.

2. Background Art

Tafamidis can stabilize the transthyretin (TTR), prevents dissociation of the natural TTR tetramer into monomers, inhibits TTR amyloid fibril formation, and is used in treating transthyretin-mediated amyloidosis. Tafamidis is developed by Pfizer and is marketed in the US as VYNDAMAX since 2019.

The chemical name of tafamidis (hereinafter referred to as "Compound I") is 6-carboxy-2-(3, 5-dichlorophenyl)-benzoxazole, and the structure is shown as follows:

Compound I

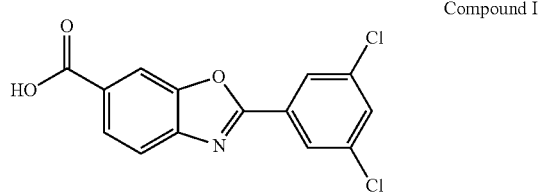 [SMILES: O=C(O)c1ccc2nc(-c3cc(Cl)cc(Cl)c3)oc2c1]

A crystalline form is a solid material whose constituents are arranged in a highly ordered microscopic structure, forming a crystal lattice that extends in all directions. Polymorphism is the ability of a compound to exist in two or more than two crystalline forms. Different crystalline forms have different physicochemical properties and can affect drug's in vivo dissolution and absorption, which will further affect drug's clinical efficacy and safety to some extent. In particular, for poorly soluble drugs, the above effects of the crystalline form will be greater. Therefore, drug polymorphism is an important part of drug research and an important part of drug quality control.

According to "FDA Regulatory Classification of Pharmaceutical Co-Crystals Guidance for Industry", pharmaceutical co-crystals are crystalline materials composed of two or more different molecules (one of which is the API) in a defined stoichiometric ratio within the same crystal lattice that are associated by nonionic and noncovalent bonds. Pharmaceutical co-crystals have provided opportunities for engineering solid-state forms beyond conventional solid-state forms of an API, such as salts and polymorphs. Pharmaceutical co-crystals can be tailored to enhance drug product bioavailability and stability and to enhance the processability of APIs during drug product manufacture. Another advantage of co-crystals is that they generate a diverse array of solid-state forms for APIs that lack ionizable functional groups, a prerequisite for salt formation.

WO2016038500 discloses Forms 1/2/4/6 of Compound I, wherein Form 2 is a tetrahydrofuran solvate, Forms 4/6 are unstable, thus Forms 2/4/6 are unsuitable for drug development. Form 1 is more stable than Forms 2/4/6, while the inventors of the present disclosure found that Form 1 has low solubility. WO2019175263 discloses an acetic acid solvate and a crystalline form of Compound I, while the inventors of the present disclosure found that the crystalline form of Compound I is unstable in drug product.

In order to overcome the disadvantages of the prior art, the inventors of the present disclosure provide fumaric acid co-crystal, glutaric acid co-crystal and adipic acid co-crystal of Compound I, which have advantages in physiochemical properties, formulation processability and bioavailability, for example, have advantages in at least one aspect of melting point, solubility, hygroscopicity, purification ability, stability, adhesiveness, compressibility, flowability, in vitro and in vivo dissolution, and bioavailability, etc. In particular, the fumaric acid co-crystal, glutaric acid co-crystal and adipic acid co-crystal of Compound I have good stability, high solubility, low hygroscopicity, high dissolution, which solve the problems in the prior arts and are of great significance for the development of drugs containing tafamidis.

SUMMARY OF THE INVENTION

The main objective of the present disclosure is to provide novel crystalline forms of tafamidis, processes for preparation and use thereof.

According to the objective of the present disclosure, co-crystal form CSV of Compound I and fumaric acid is provided (hereinafter referred to as Form CSV).

According to one aspect of the present disclosure, the X-ray powder diffraction pattern of Form CSV shows characteristic peaks at 2theta values of 13.4°±0.2°, 22.8°±0.2° and 20.8°±0.2° using CuKα radiation.

Furthermore, the X-ray powder diffraction pattern of Form CSV shows one or two or three characteristic peaks at 2theta values of 18.0°±0.2°, 16.5°±0.2° and 9.6°±0.2°. Preferably, the X-ray powder diffraction pattern of Form CSV shows three characteristic peaks at 2theta values of 18.0°±0.2°, 16.5°±0.2° and 9.6°±0.2°.

Furthermore, the X-ray powder diffraction pattern of Form CSV shows one or two or three characteristic peaks at 2theta values of 15.6°±0.2°, 19.2°±0.2° and 23.9°±0.2°. Preferably, the X-ray powder diffraction pattern of Form CSV shows three characteristic peaks at 2theta values of 15.6°±0.2°, 19.2°±0.2° and 23.9°±0.2°.

According to another aspect of the present disclosure, the X-ray powder diffraction pattern of Form CSV shows three or four or five or six or seven or eight or nine characteristic peaks at 2theta values of 13.4°±0.2°, 22.8°±0.2°, 20.8°±0.2°, 18.0°±0.2°, 16.5°±0.2°, 9.6°±0.2°, 15.6°±0.2°, 19.2°±0.2° and 23.9°±0.2° using CuKα radiation.

Without any limitation being implied, Form CSV is an anhydrate.
Without any limitation being implied, the molar ratio of Compound I and fumaric acid in Form CSV is 1:0.5.

Without any limitation being implied, the X-ray powder diffraction pattern of Form CSV is substantially as depicted in FIG. 1.

Without any limitation being implied, the thermo gravimetric analysis curve of Form CSV is substantially as depicted in FIG. 2, which shows about 0.2% weight loss when heated to 150° C. The curve shows about 16.2% weight loss when heated from 150° C. to 225° C., corresponding to the loss of fumaric acid.

Without any limitation being implied, the differential scanning calorimetry curve of Form CSV is substantially as depicted in FIG. 6, which shows an endothermic peak when heated to 265.2° C. (onset temperature).

According to the objective of the present disclosure, a process for preparing Form CSV is also provided. The process comprises: adding tafamidis and fumaric acid into a ketone, an ester, an ether, or a mixture of an alcohol and an ether, stirring to obtain crystalline form CSV.

Furthermore, the molar ratio of fumaric acid and Compound I is preferably 1:1-3:1.

Furthermore, said ketone is preferably acetone, said ester is preferably ethyl acetate, said ether are preferably anisole and tetrahydrofuran, said alcohol is preferably n-butyl alcohol.

Furthermore, said stirring temperature is preferably 0-60° C., said stirring time is preferably 3-10 days.

Form CSV of the present disclosure has the following advantages:

(1) Compared with prior art, Form CSV has higher solubility. In particular, in FeSSIF (Fed state simulated intestinal fluids), the solubility of Form CSV is 10 times that of WO2016038500 Form 1.

Compound I is a poorly water-soluble drug and belongs to BCS IV. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Compared with prior art, Form CSV has better in vitro dissolution. In pH6.8 Phosphate Buffer Saline (PBS), the dissolution of Form CSV drug product is higher than that of WO2016038500 Form 1.

Drug with different crystalline forms may lead to different in vivo dissolution rates, which directly affects drug's in vivo absorption, distribution, excretion and metabolism, and finally leads to difference in clinical efficacy due to different bioavailability. Dissolution is an important prerequisite for drug absorption. Good in vitro dissolution leads to higher in vivo absorption, better in vivo exposure, thereby improving drug's bioavailability and efficacy.

(3) Form CSV of the present disclosure has low hygroscopicity. The test result shows that the weight gain of Form CSV at 80% RH (Relative humidity) is 0.09%. Form CSV is non-hygroscopic or almost non-hygroscopic.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts strict requirements on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic value.

(4) Form CSV drug substance and drug product of the present disclosure have good stability. Crystalline state of Form CSV drug substance doesn't change for at least six months when stored under the condition of 25° C./60% RH. The chemical purity is above 99.9% and remains substantially unchanged during storage. After Form CSV is mixed with the excipients to form a drug product and stored under the condition of 25° C./60% RH, crystalline state of Form CSV drug product doesn't change for at least three months. These results show that Form CSV drug substance and product have good stability under long-term storage conditions, which is beneficial to drug storage.

Meanwhile, crystalline state of Form CSV drug substance doesn't change for at least six months when stored under the condition of 40° C./75% RH. The crystalline state of Form CSV drug substance doesn't change for at least two months when stored under the condition of 60° C./75% RH. The chemical purity is above 99.9% and remains substantially unchanged during storage. After Form CSV is mixed with the excipients to form a drug product and stored under the condition of 40° C./75% RH, crystalline state of Form CSV drug product doesn't change for at least three months. These results show that Form CSV drug substance and product have good stability under accelerated and stress conditions. Good stability under accelerated and stress conditions is of great importance to the drug development. Drug substance and drug product will go through high temperature and high humidity conditions caused by weather, season and regional climate differences during storage, transportation, and manufacturing processes. Form CSV drug substance and product have good stability under these stress conditions, which is beneficial to avoid the influence on drug quality when not stored in condition recommended in label.

Meanwhile, Form CSV has good mechanical stability. Form CSV has good physical stability after grinding. Grinding and pulverization are often required in the drug manufacturing process. Good physical stability of the drug substance can reduce the risk of crystallinity decrease and crystal transformation during the drug production process.

Crystalline transformation can lead to changes in the absorption of the drug, affect bioavailability, and even cause toxicity and side effects. Good chemical stability ensures that no impurities are generated during storage. Form CSV has good physical and chemical stability, ensuring consistent and controllable quality of the drug substance and drug product, and minimizing change in quality, bioavailability and toxicity due to crystal transformation or impurity generation. Furthermore, Form CSV of the present disclosure also has the following advantages:

(1) Compared with prior art, Form CSV of the present disclosure has better compressibility. Failure in hardness/friability test and tablet crack issue can be avoided due to better compressibility of Form CSV, making the preparation process more reliable, improving product appearance and product quality. Better compressibility can increase the compression rate, further increases the efficiency of process and reduces the cost of compressibility improving excipients. According to the objective of the present disclosure, co-crystal form CSVI of Compound I and glutaric acid is provided (hereinafter referred to as Form CSVI).

According to one aspect of the present disclosure, the X-ray powder diffraction pattern of Form CSVI shows characteristic peaks at 2theta values of 14.1°±0.2°, 19.1°±0.2° and 17.2°±0.2° using CuKα radiation.

Furthermore, the X-ray powder diffraction pattern of Form CSVI shows one or two or three characteristic peaks at 2theta values of 10.0°±0.2°, 22.5°±0.2° and 24.3°±0.2°. Preferably, the X-ray powder diffraction pattern of Form CSVI shows three characteristic peaks at 2theta values of 10.0°±0.2°, 22.5°±0.2° and 24.3°±0.2°.

Furthermore, the X-ray powder diffraction pattern of Form CSVI shows one or two or three or four characteristic peaks at 2theta values of 34.1°±0.2°, 33.4°±0.2°, 11.2°±0.2° and 35.5°±0.2°. Preferably, the X-ray powder diffraction pattern of Form CSVI shows four characteristic peaks at 2theta values of 34.1°±0.2°, 33.4°±0.2°, 11.2°±0.2° and 35.5°±0.2°.

According to another aspect of the present disclosure, the X-ray powder diffraction pattern of Form CSVI shows three or four or five or six or seven or eight or nine or ten characteristic peaks at 2theta values of 14.1°±0.2°, 19.1°±0.2°, 17.2°±0.2°, 10.0°±0.2°, 22.5°±0.2°, 24.3°±0.2° 34.1°±0.2°, 33.4°±0.2°, 11.2°±0.2° and 35.5°±0.2° using CuKα radiation.

Without any limitation being implied, the X-ray powder diffraction pattern of Form CSVI is substantially as depicted in FIG. 15.

Without any limitation being implied, the thermo gravimetric analysis curve of Form CSVI is substantially as depicted in FIG. 17, which shows about 17.5% weight loss when heated to 200° C., corresponding to the loss of glutaric acid.

Without any limitation being implied, the differential scanning calorimetry curve of Form CSVI is substantially as depicted in FIG. 18, which shows an endothermic peak when heated to 166.6° C. (onset temperature).

According to the objective of the present disclosure, a process for preparing Form CSVI is also provided. The process comprises: adding tafamidis and glutaric acid into an ester, stirring to obtain crystalline form CSVI.

Furthermore, the molar ratio of glutaric acid and Compound I is preferably 2:1-3:1.

Furthermore, said ester is preferably ethyl acetate.

Furthermore, said stirring temperature is preferably 0-40° C., said stirring time is preferably 3-10 days.

Form CSVI of the present disclosure has the following advantages:

(1) Compared with prior art, Form CSVI has higher solubility.

Compound I is a poorly water-soluble drug and belongs to BCS IV. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Compared with prior art, Form CSVI has better in vitro dissolution. In pH6.8 PBS+1% Tween 80 and pH6.8 PBS+3% Tween 80, the dissolution of Form CSVI drug product is higher than that of WO2016038500 Form 1.

Drug with different crystalline forms may lead to different in vivo dissolution rates, which directly affects drug's in vivo absorption, distribution, excretion and metabolism, and finally leads to difference in clinical efficacy due to different bioavailability. Dissolution is an important prerequisite for drug absorption. Good in vitro dissolution leads to higher in vivo absorption, better in vivo exposure, thereby improving drug's bioavailability and efficacy.

(3) Form CSVI of the present disclosure has low hygroscopicity. The test result shows that the weight gain of Form CSVI at 80% RH is 0.21%. Form CSVI is slightly hygroscopic.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts strict requirements on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic value.

(4) Form CSVI drug substance of the present disclosure has good stability. Crystalline state of Form CSVI drug substance doesn't change for at least six months when stored under the condition of 25° C./60% RH. The chemical purity is above 99.9% and remains substantially unchanged during storage. The result shows that Form CSVI drug substance has good stability under long-term storage conditions, which is beneficial to drug storage.

Meanwhile, crystalline state of Form CSVI drug substance doesn't change for at least six months when stored under the condition of 40° C./75% RH. The crystalline state of Form CSVI drug substance doesn't change for at least two months when stored under the condition of 60° C./75% RH. The chemical purity is above 99.9% and remains substantially unchanged during storage. These results show that Form CSVI drug substance has good stability under accelerated and stress conditions. Good stability under accelerated and stress conditions is of great importance to the drug development. Drug substance will go through high temperature and high humidity conditions caused by weather, season and regional climate differences during storage, transportation, and manufacturing processes. Form CSVI drug substance has good stability under these stress conditions, which is beneficial to avoid the influence on drug quality when not stored in condition recommended in label.

Crystalline transformation can lead to changes in the absorption of the drug, affect bioavailability, and even cause toxicity and side effects. Good chemical stability ensures that no impurities are generated during storage. Form CSVI has good physical and chemical stability, ensuring consistent and controllable quality of the drug substance and drug product, and minimizing change in quality, bioavailability and toxicity due to crystal transformation or impurity generation.

According to the objective of the present disclosure, co-crystal form CSVII of Compound I and adipic acid is provided (hereinafter referred to as Form CSVII).

According to one aspect of the present disclosure, the X-ray powder diffraction pattern of Form CSVII shows characteristic peaks at 2theta values of 13.9°±0.2°, 18.8°±0.2° and 25.6°±0.2° using CuKα radiation.

Furthermore, the X-ray powder diffraction pattern of Form CSVII shows one or two or three characteristic peaks at 2theta values of 24.1°±0.2°, 11.3°±0.2°, and 22.7°±0.2°. Preferably, the X-ray powder diffraction pattern of Form CSVII shows three characteristic peaks at 2theta values of 24.1°±0.2°, 11.3°±0.2°, and 22.7°±0.2°.

Furthermore, the X-ray powder diffraction pattern of Form CSVII shows one or two or three characteristic peaks at 2theta values of 17.2°±0.2°, 9.8°±0.2°, and 17.0°±0.2°. Preferably, the X-ray powder diffraction pattern of Form CSVII shows three characteristic peaks at 2theta values of 17.2°±0.2°, 9.8°±0.2°, and 17.0°±0.2°.

According to another aspect of the present disclosure, the X-ray powder diffraction pattern of Form CSVII shows three or four or five or six or seven or eight or nine characteristic peaks at 2theta values of 13.9°±0.2°, 18.8°±0.2°, 25.6°±0.2°, 24.1°±0.2°, 11.3°±0.2°, 22.7°±0.2°, 17.2°±0.2°, 9.8°±0.2°, and 17.0°±0.2° using CuKα radiation.

Without any limitation being implied, the X-ray powder diffraction pattern of Form CSVII is substantially as depicted in FIG. 25.

Without any limitation being implied, the thermo gravimetric analysis curve of Form CSVII is substantially as depicted in FIG. 26, which shows about 19.0% weight loss when heated to 200° C., corresponding to the loss of adipic acid.

Without any limitation being implied, the differential scanning calorimetry curve of Form CSVII is substantially as depicted in FIG. 27, which shows an endothermic peak when heated to 166.7° C. (onset temperature).

According to the objective of the present disclosure, a process for preparing Form CSVII is also provided. The process comprises: adding tafamidis and adipic acid into an ester, stirring to obtain crystalline form CSVII.

Furthermore, the molar ratio of adipic acid and Compound I is preferably 1:1-3:1.

Furthermore, said ester is preferably ethyl acetate.

Furthermore, said stirring temperature is preferably 20-60° C., said stirring time is preferably 3-10 days.

Form CSVII of the present disclosure has the following advantages:

(1) Compared with prior art, Form CSVII has higher solubility. In particular, in SGF (Simulated gastric fluids), the solubility of Form CSVII is 12 times higher than that of WO2016038500 Form 1. Compound I is a poorly water-soluble drug and belongs to BCS IV. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Compared with prior art, Form CSVII has better in vitro dissolution. In pH6.8 PBS+1% Tween 80, the dissolution of Form CSVII drug product is higher than that of WO2016038500 Form 1.

Drug with different crystalline forms may lead to different in vivo dissolution rates, which directly affects drug's in vivo absorption, distribution, excretion and metabolism, and finally leads to difference in clinical efficacy due to different bioavailability. Dissolution is an important prerequisite for drug absorption. Good in vitro dissolution leads to higher in vivo absorption, better in vivo exposure, thereby improving drug's bioavailability and efficacy.

(3) Form CSVII of the present disclosure has low hygroscopicity. The test result shows that the weight gain of Form CSVII at 80% RH is 0.04%. Form CSVII is non hygroscopic or almost non hygroscopic.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts strict requirements on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic value.

(4) Form CSVII drug substance of the present disclosure has good stability. Crystalline state of Form CSVII drug substance doesn't change for at least three months when stored under the condition of 25° C./60% RH. The chemical purity is above 99.9% and remains substantially unchanged during storage. After Form CSVII is mixed with the excipients to form a drug product and stored under the condition of 30° C./60% RH, crystalline state of Form CSVII drug product doesn't change for at least three months. These results show that Form CSVII drug substance and product have good stability under long-term storage conditions, which is beneficial to drug storage. Meanwhile, crystalline state of Form CSVII drug substance doesn't change for at least three months when stored under the condition of 40° C./75% RH. The crystalline state of Form CSVII drug substance doesn't change for at least two months when stored under the condition of 60° C./75% RH. The chemical purity is above 99.9% and remains substantially unchanged during storage. These results show that Form CSVII drug substance has good stability under accelerated and stress conditions. Good stability under accelerated and stress conditions is of great importance to the drug development. Drug substance will go through high temperature and high humidity conditions caused by weather, season and regional climate differences during storage, transportation, and manufacturing processes. Form CSVII drug substance has good stability under these stress conditions, which is beneficial to avoid the influence on drug quality when not stored in condition recommended in label.

Crystalline transformation can lead to changes in the absorption of the drug, affect bioavailability, and even cause toxicity and side effects. Good chemical stability ensures that no impurities are generated during storage. Form CSVII has good physical and chemical stability, ensuring consistent and controllable quality of the drug substance and drug product, and minimizing change in quality, bioavailability and toxicity due to crystal transformation or impurity generation. Furthermore, Form CSVII of the present disclosure also has the following advantages:

(1) Compared with prior art, Form CSVII of the present disclosure has better compressibility. Failure in hardness/friability test and tablet crack issue can be avoided due to better compressibility of Form CSVII, making the preparation process more reliable, improving product appearance and product quality. Better compressibility can increase the compression rate, further increases the efficiency of process and reduces the cost of compressibility improving excipients.

(2) Compared with prior art, Form CSVII of the present disclosure shows superior adhesiveness. Adhesiveness evaluation results indicate that adhesion quantity of Form CSVII is remarkably lower than that of prior art form. Due to superior adhesiveness of Form CSVII, adhesion to roller and tooling during dry-granulation and compression process can be reduced, which is also beneficial to improve product appearance and weight variation. In addition, superior adhesiveness of Form CSVII can reduce the agglomeration of drug substance, which is beneficial to the dispersion of drug substance and reduce the adhesion between drug substance and other instruments, and improve the blend uniformity and content uniformity of drug product. According to the objective of the present disclosure, a pharmaceutical composition is provided, said pharmaceutical composition comprises a therapeutically effective amount of Form CSV, Form CSVI or Form CSVII and pharmaceutically acceptable carriers or excipients.

Furthermore, Form CSV, Form CSVI or Form CSVII can be used for preparing drugs treating disease caused by transthyretin-mediated amyloidosis.

Furthermore, Form CSV, Form CSVI or Form CSVII can be used for preparing drugs treating transthyretin-mediated amyloidosis and/or transthyretin amyloid cardiomyopathy.

In the present disclosure, said "stirring" is accomplished by using a conventional method in the field such as magnetic stirring or mechanical stirring and the stirring speed is 50 to 1800 r/min, preferably the magnetic stirring speed is 300 to 900 r/min and mechanical stirring speed is 100 to 300 r/min. Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, forced air convection oven or vacuum oven.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sample preparation and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions. Therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be considered. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exact same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CSV, Form CSVI and Form CSVII of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

DESCRIPTION OF PREFERRED EMBODIMENTS

Figure 1:
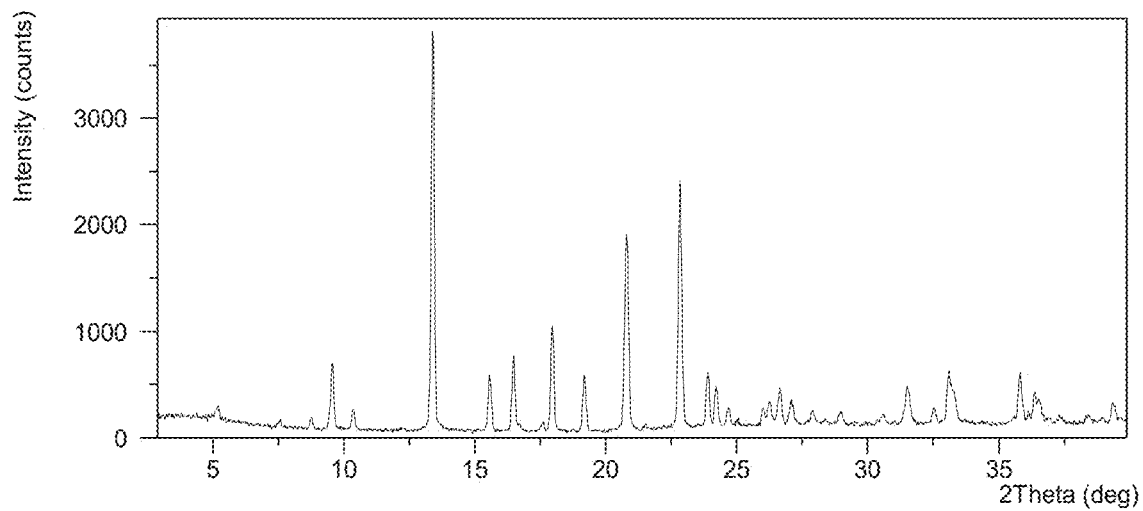
FIG. 1 shows an XRPD pattern of Form CSV in Example 1.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:

XRPD: X-ray Powder Diffraction

DSC: Differential Scanning calorimetry

TGA: Thermo Gravimetric Analysis

DVS: Dynamic Vapor Sorption $^1$H NMR: Proton Nuclear Magnetic Resonance

UPLC: Ultra Performance Liquid Chromatography

Instruments and Methods Used for Data Collection:

X-ray powder diffraction patterns in the present disclosure (except XRPD patterns of drug product stability study) were acquired by a Bruker D2 PHASER X-ray powder diffractometer. The parameters of the X-ray powder diffraction method of the present disclosure are as follows:

X-ray reflection: Cu, Kα

Kα1 (Å): 1.54060. Kα2 (Å): 1.54439

Kα2/Kα1 intensity ratio: 0.50

X-ray powder diffraction patterns of drug product stability study in the present disclosure were acquired by a Bruker D8 Discover X-ray powder diffractometer. The parameters of the X-ray powder diffraction method of the present disclosure are as follows:

X-ray reflection: Cu, Kα

Kα1 (Å): 1.54056. Kα2 (Å): 1.54439

Kα2/Kα1 intensity ratio: 0.50

Voltage: 40 (kV)

Current: 40 (mA)

Scan range (2θ): from 4.0 degree to 40.0 degree

Differential scanning calorimetry (DSC) data in the present disclosure were acquired by a TA Q2000. The parameters of the DSC method of the present disclosure were as follows:

Heating rate: 10° C./min

Purge gas: nitrogen

Thermo gravimetric analysis (TGA) data in the present disclosure were acquired by a TA Q500. The parameters of the TGA method of the present disclosure were as follows:

Heating rate: 10° C./min

Purge gas: nitrogen

Dynamic Vapor Sorption (DVS) is measured via a SMS (Surface Measurement Systems Ltd.) intrinsic DVS instrument. Its control software is DVS-Intrinsic control software. Typical parameters for DVS tests are as follows:

Temperature: 25° C.

Gas and flow rate: $N_2$, 200 mL/min dm/dt: 0.002%/min

RH range: 0% RH to 95% RH

Proton nuclear magnetic resonance spectrum data ($^1$H NMR) were collected from a Bruker Avance II DMX 400M HZ NMR spectrometer. 1-5 mg of sample was weighed and dissolved in 0.5 mL of deuterated dimethyl sulfoxide to obtain a solution with a concentration of 2-10 mg/mL. The UPLC parameters for dynamic solubility tests in the present disclosure are shown in Table 1.

TABLE 1

| UPLC | Waters UPLC H-Class with DAD detector | |
|---|---|---|
| Column | Waters ACQUITY UPLC BEH $C_{18}$, 2.1 × 50 mm, 1.7 μm | |
| Mobile Phase | A: 0.1% trifluoroacetic acid aqueous solution B: 0.1% trifluoroacetic acid acetonitrile solution | |
| Gradient | Time (min) | % A |
| | 0.0 | 95.0 |
| | 1.0 | 95.0 |
| | 3.0 | 30.0 |
| | 5.0 | 10.0 |
| | 5.1 | 95.0 |
| | 7.0 | 95.0 |
| Running time | 7.0 min | |
| Equilibrium time | 0.0 min | |
| Speed | 0.5 mL/min | |
| Injection Volume | 1 μL | |
| Detection wavelength | UV at 290 nm | |
| Column Temperature | 40° C. | |
| Sample Temperature | Room temperature | |
| Diluent | Methanol | |

The UPLC parameters for purity tests in the present disclosure are shown in Table 2.

TABLE 2

| UPLC | Waters UPLC H-Class with DAD detector | |
|---|---|---|
| Column | ACE Excel 2 Super $C_{18}$ 3.0 × 100 mm, 2.0 μm | |
| Mobile Phase | A: Acetonitrile: water (pH 3.0, $H_3PO_4$) = 5:95 B: Acetonitrile | |
| Gradient | Time (min) | % A |
| | 0.0 | 40 |
| | 0.5 | 40 |
| | 5.0 | 20 |
| | 7.0 | 10 |
| | 12.0 | 10 |
| | 12.1 | 40 |
| | 18.0 | 40 |

TABLE 2-continued

| | |
|---|---|
| Running time | 18.0 min |
| Equilibrium time | 0.0 min |
| Speed | 0.5 mL/min |
| Injection Volume | 1 μL |
| Detection wavelength | UV at 210 nm |
| Column Temperature | 40° C. |
| Sample Temperature | Room Temperature |
| Diluent | Methanol |

The UPLC parameters for drug product dissolution tests in the present disclosure are shown in Table 3.

TABLE 3

| | |
|---|---|
| UPLC | Waters UPLC H-Class with DAD detector |
| | Waters ACQUITY UPLC BEH |
| Column | $C_{18}$ 2.1 × 50 mm, 1.7 μm |
| Mobile Phase | A: 0.1% trifluoroacetic acid aqueous solution |
| | B: 0.1% trifluoroacetic acid acetonitrile solution |
| Gradient | Time (min)    % A |

| Time (min) | % A |
|---|---|
| 0 | 95 |
| 1.0 | 95 |
| 3.0 | 30 |
| 5.0 | 10 |
| 5.1 | 95 |
| 7.0 | 95 |

| | |
|---|---|
| Running time | 7.0 min |
| Equilibrium time | 0.0 min |
| Speed | 0.5 mL/min |
| Injection Volume | 1 μL |
| Detection wavelength | UV at 290 nm |
| Column Temperature | 40° C. |
| Sample Temperature | Room Temperature |
| Diluent | Methanol |

Unless otherwise specified, the following examples were conducted at room temperature. Said "room temperature" is not a specific temperature, but a temperature range of 10-30° C. According to the present disclosure, compound I used as a raw material includes but not limited to solid (crystalline or amorphous), oil, liquid and solution. Preferably, compound I as a raw material is solid.

Compound I used in the following examples can be prepared by known methods in the prior art, for example, the method disclosed in WO2016038500.

EXAMPLES

Example 1 Preparation of Form CSV 252.6 mg of fumaric acid was weighed into a glass vial, and then 18.0 mL of acetone and 312.0 mg of tafamidis free acid were added to form a suspension. The suspension was stirred at room temperature for about 5 days. After separation, the obtained solid was vacuum dried at 25° C. for about one hour. 268.8 mg of the dried sample was weighed into another glass vial. 5.0 mL of water was added, and the suspension was stirred at room temperature for about one hour. Then, 4.0 mL of water was added and the suspension was stirred overnight. A crystalline solid was obtained after separation and vacuum drying at 50° C. The obtained solid was confirmed to be Form CSV by XRPD. The XRPD pattern is substantially as depicted in FIG. 1, and the XRPD data are listed in Table 4.

Figure 2:
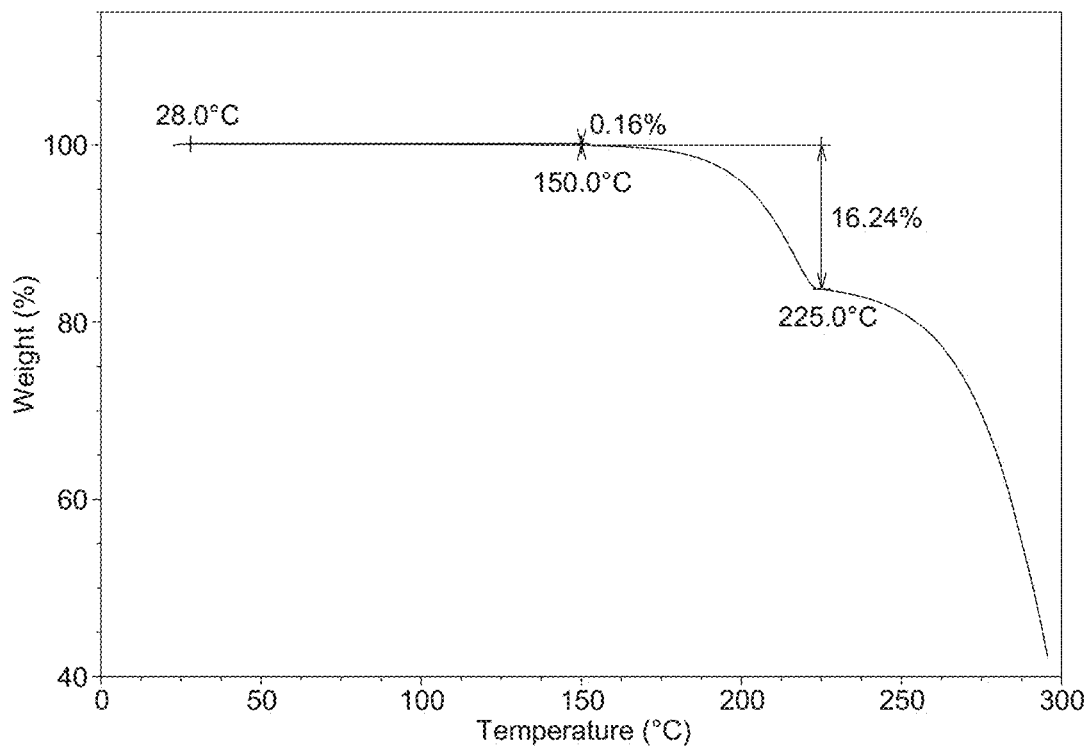
FIG. 2 shows a TGA curve of Form CSV in Example 1.

The TGA curve of Form CSV depicted in FIG. 2 shows about 0.2% weight loss when heated to 150° C., and about 16.2% weight loss when heated from 150° C. to 225° C., which corresponds to the loss of fumaric acid.

Figure 3:
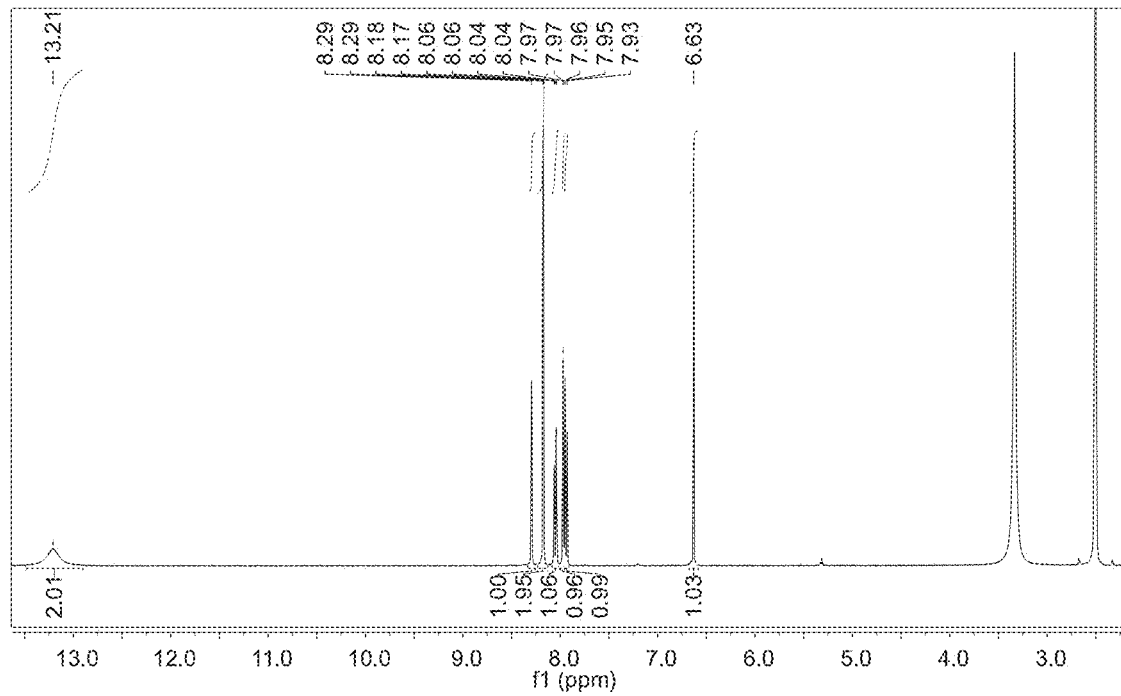
FIG. 3 shows a $^1$H NMR spectrum of Form CSV in Example 1.

The $^1$H NMR spectrum of Form CSV is substantially as depicted in FIG. 3, which complies with Compound I. The chemical shift at δ=6.63 is the characteristic peaks of fumaric acid. The $^1$H NMR spectrum indicates that in Form CSV, the molar ratio of tafamidis and fumaric acid equals 1:0.5. The corresponding data are: $^1$H NMR (400 MHz, DMSO) δ 13.21 (s, 2H), 8.29 (d, J=1.0 Hz, 1H), 8.17 (d, J=1.9 Hz, 2H), 8.05 (dd, J=8.4, 1.5 Hz, 1H), 7.97 (t, J=1.9 Hz, 1H), 7.94 (d, J=8.3 Hz, 1H), 6.63 (s, 1H).

TABLE 4

| 2θ | d spacing | Intensity % |
|---|---|---|
| 5.16 | 17.11 | 3.17 |
| 7.54 | 11.73 | 1.27 |
| 8.74 | 10.11 | 2.46 |
| 9.55 | 9.26 | 16.17 |
| 10.35 | 8.54 | 4.80 |
| 13.39 | 6.61 | 100.00 |
| 15.55 | 5.70 | 13.79 |
| 16.47 | 5.38 | 18.61 |
| 17.58 | 5.04 | 1.91 |
| 17.95 | 4.94 | 25.21 |
| 19.17 | 4.63 | 13.94 |
| 20.78 | 4.27 | 48.53 |
| 21.50 | 4.13 | 1.54 |
| 22.82 | 3.90 | 61.97 |
| 23.88 | 3.73 | 14.37 |
| 24.20 | 3.68 | 11.14 |
| 24.68 | 3.61 | 5.59 |
| 25.98 | 3.43 | 5.70 |
| 26.24 | 3.40 | 7.05 |
| 26.63 | 3.35 | 10.57 |
| 27.07 | 3.29 | 7.40 |
| 27.88 | 3.20 | 5.01 |
| 28.96 | 3.08 | 4.80 |
| 30.56 | 2.93 | 4.01 |
| 31.50 | 2.84 | 10.61 |
| 32.51 | 2.75 | 5.58 |
| 33.08 | 2.71 | 15.03 |
| 35.79 | 2.51 | 14.59 |
| 36.35 | 2.47 | 9.47 |
| 36.55 | 2.46 | 7.21 |
| 37.33 | 2.41 | 3.35 |
| 38.37 | 2.35 | 3.82 |
| 39.33 | 2.29 | 6.84 |

Example 2 Preparation of Form CSV 14.1 mg of tafamidis free acid and 12.0 mg of fumaric acid were weighed into a glass vial, and 1.0 mL of acetone was added to form a suspension. The suspension was stirred at room temperature for about 7 days. A crystalline solid was obtained by separation.

Figure 4:
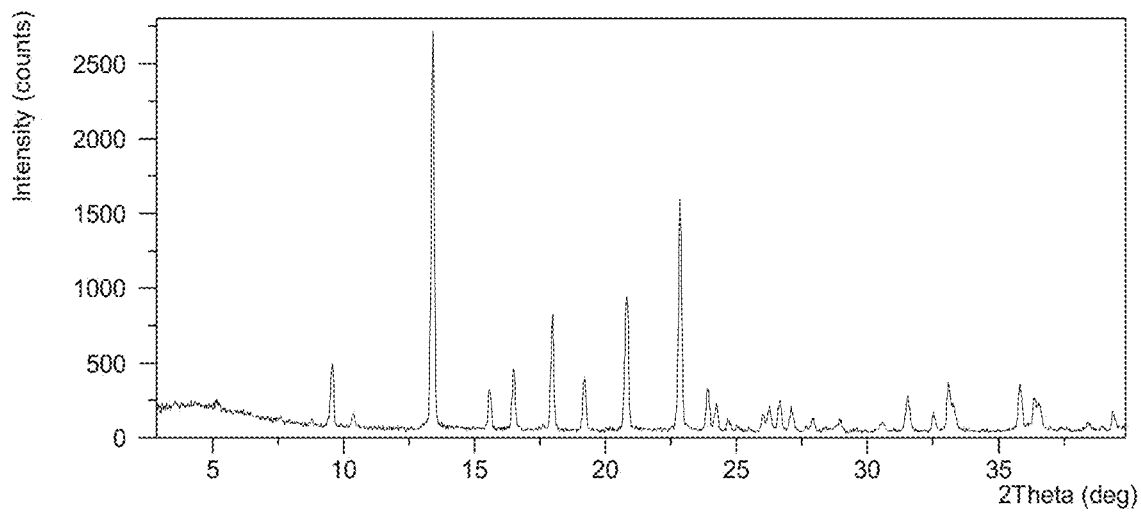
FIG. 4 shows an XRPD pattern of Form CSV in Example 2.

The obtained solid was confirmed to be Form CSV by XRPD. The XRPD pattern is substantially as depicted in FIG. 4, and the XRPD data are listed in Table 5.

TABLE 5

| 2θ | d spacing | Intensity % |
|---|---|---|
| 5.14 | 17.18 | 2.35 |
| 9.56 | 9.25 | 15.03 |
| 10.38 | 8.52 | 3.25 |
| 13.40 | 6.61 | 100.00 |
| 15.57 | 5.69 | 9.66 |
| 16.48 | 5.38 | 15.15 |
| 17.96 | 4.94 | 28.85 |
| 19.18 | 4.63 | 12.90 |
| 20.80 | 4.27 | 33.22 |
| 22.83 | 3.90 | 57.30 |
| 23.89 | 3.72 | 10.53 |

TABLE 5-continued

| 2θ | d spacing | Intensity % |
|---|---|---|
| 24.22 | 3.67 | 6.89 |
| 24.66 | 3.61 | 3.08 |
| 26.00 | 3.43 | 3.99 |
| 26.25 | 3.40 | 6.04 |
| 26.65 | 3.35 | 7.52 |
| 27.09 | 3.29 | 5.32 |
| 27.90 | 3.20 | 3.22 |
| 28.94 | 3.09 | 2.80 |
| 30.55 | 2.93 | 2.09 |
| 31.51 | 2.84 | 8.58 |
| 32.50 | 2.76 | 4.18 |
| 33.08 | 2.71 | 11.75 |
| 35.80 | 2.51 | 12.00 |
| 36.36 | 2.47 | 7.84 |
| 36.57 | 2.46 | 5.93 |
| 38.40 | 2.34 | 2.12 |
| 39.34 | 2.29 | 4.63 |

Figure 5:
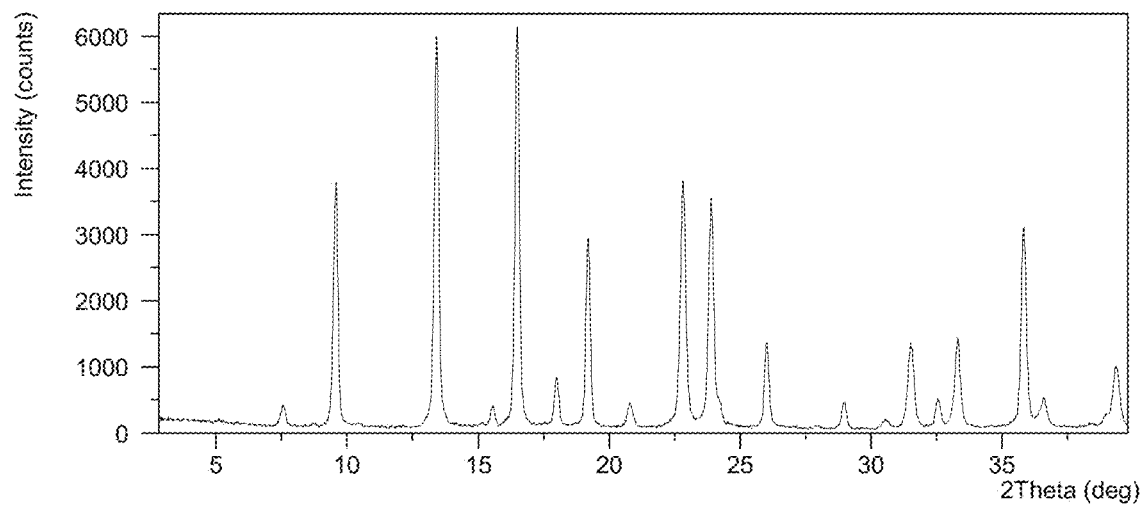
FIG. 5 shows an XRPD pattern of Form CSV in Example 3.

Example 3 Preparation of Form CSV 5.02 g of tafamidis free acid, 1.88 g of fumaric acid and about 250 mL of n-butanol/anisole (1:4, v/v) solvent were added into the reactor and the system was mechanically stirred. When heated to 100° C., a clear solution was obtained. The solution was cooled to 85° C. and about 10.0 mg of Form CSV seeds were added. After aging for about 15 minutes, the suspension was cooled to 5° C. and filtered. The wet cake was vacuum dried at 50° C. and a crystalline solid was obtained. The obtained solid was confirmed to be Form CSV by XRPD. The XRPD pattern is substantially as depicted in FIG. 5, and the XRPD data are listed in Table 6.

TABLE 6

| 2θ | d spacing | Intensity % |
|---|---|---|
| 7.56 | 11.69 | 4.89 |
| 9.59 | 9.23 | 57.47 |
| 13.40 | 6.61 | 97.83 |
| 15.58 | 5.69 | 4.44 |
| 16.48 | 5.38 | 100.00 |
| 17.96 | 4.94 | 12.03 |
| 19.18 | 4.63 | 47.28 |
| 20.78 | 4.27 | 5.87 |
| 22.80 | 3.90 | 61.95 |
| 23.89 | 3.72 | 56.64 |
| 26.00 | 3.43 | 21.18 |
| 28.98 | 3.08 | 6.69 |
| 30.58 | 2.92 | 2.05 |
| 31.51 | 2.84 | 20.40 |
| 32.56 | 2.75 | 7.48 |
| 33.32 | 2.69 | 20.99 |
| 35.78 | 2.51 | 47.09 |
| 36.58 | 2.46 | 7.70 |
| 39.31 | 2.29 | 15.47 |

Figure 6:
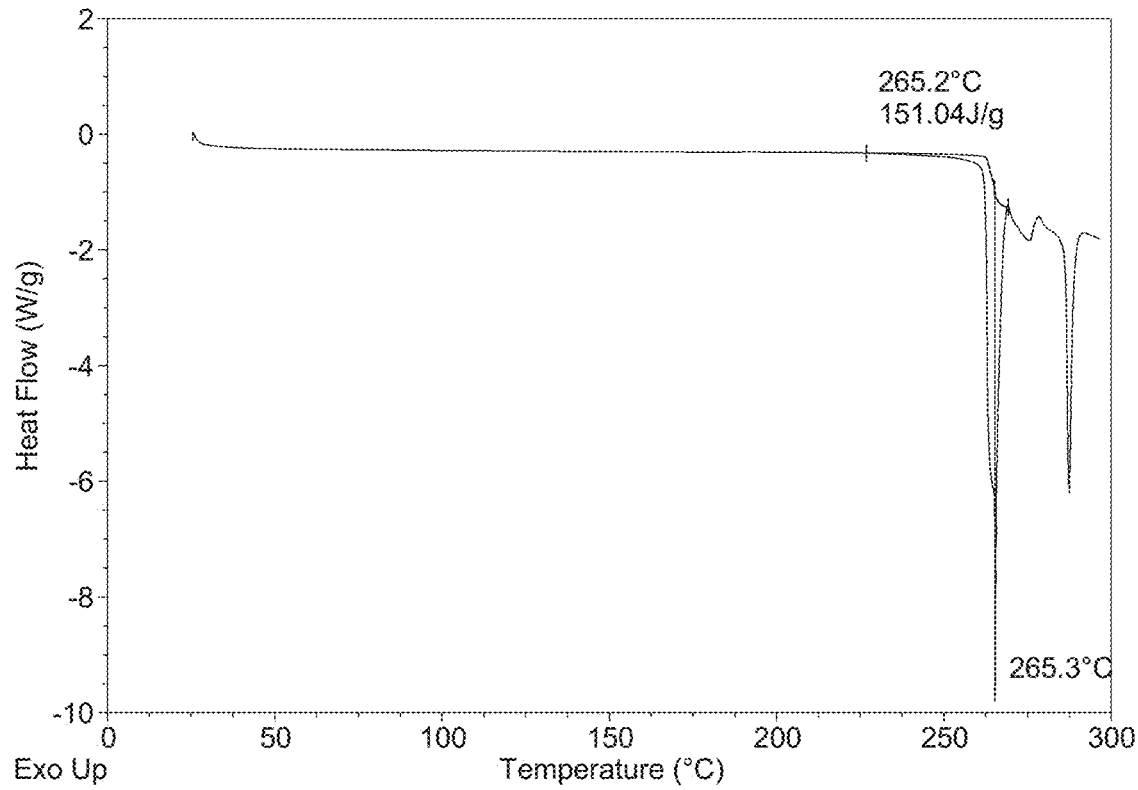
FIG. 6 shows a DSC curve of Form CSV in Example 4.

Example 4 Preparation of Form CSV 30.00 g of tafamidis free acid, 11.63 g of fumaric acid and about 1350 mL of n-butanol/anisole (1:3, v/v) solvent were added into a 2-L reactor and the system was mechanically stirred. When heated to 95° C., a clear solution was obtained. The clear solution was cooled to 85° C. and about 600.8 mg of Form CSV seeds were added. After aging for about one hour, the suspension was cooled to 5° C. in two hours then filtered. The wet cake was washed with n-heptane and vacuum dried at 50° C. to obtain a crystalline solid. The solid was confirmed to be Form CSV. The DSC curve of Form CSV is substantially as depicted in FIG. 6, which shows one endothermic peak at around 265.2° C. (onset temperature).

Example 5 Preparation of Form CSV 0.51 g of tafamidis free acid, 0.94 g of fumaric acid and 15 mL of tetrahydrofuran were added into a 50-mL reactor and the system was mechanically stirred. When heated to 60° C., a clear solution was obtained. After cooling down to 50° C., 5.3 mg of Form CSV seeds were added. After aging for about five minutes, the suspension was cooled to 25° C. and a crystalline solid was obtained. The solid was tested and confirmed to be Form CSV Example 6 Kinetic Solubility of Form CSV When solubility test is used to forecast the in vivo performance of a drug, it is critical that the in vitro test mimics the conditions in vivo as closely as possible. Simulated gastric fluid (SGF), Fed-state simulated intestinal fluid (FeSSIF) and Fasted-state simulated intestinal fluid (FaSSIF) are used to mimic the condition in vivo and forecast food effects on the orally administered drugs. Solubility in these media is close to solubility in vivo.

20 mg of Form CSV and 20 mg of WO2016038500 Form 1 were suspended into 3.0 mL of SGF, 3.0 mL of FaSSIF and 3.0 mL of FaSSIF to get saturated solutions. After equilibrated for 1 h, concentrations (μg/mL) of compound I in the saturated solutions were measured by UPLC. The results are listed in Table 7.

TABLE 7

| Medium | Form CSV | WO2016038500 Form 1 |
|---|---|---|
| SGF | 5.6 | 1.5 |
| FeSSIF | 6.0 | 0.6 |
| FaSSIF | 11.5 | 9.0 |

The results show that the solubility of Form CSV in SGF, FeSSIF and FaSSIF is higher than that of Form 1 in the prior art. In particular, in FeSSIF, the solubility of Form CSV is ten times that of WO2016038500 Form 1.

Example 7 Stability of Form CSV

Figure 7:
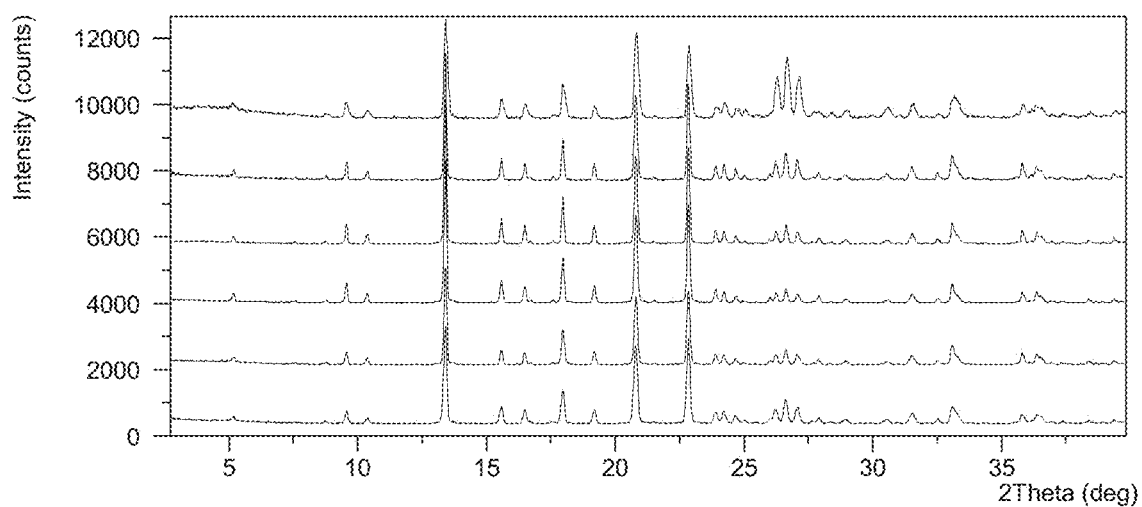
FIG. 7 shows an XRPD pattern overlay of Form CSV before and after storage (from top to bottom: stored at 60° C./75% RH (open) for two months, stored at 60° C./75% RH (sealed) for two months, stored at 40° C./75% RH (open) for six months, stored at 40° C./75% RH (sealed) for six months, stored at 25° C./60% RH (open) for six months, initial).

Approximately 5 mg of solid samples of Form CSV were stored under different conditions of 25° C./60% RH, 40° C./75% RH and 60° C./75% RH. Crystalline form and chemical impurity were checked by XRPD and HPLC, respectively. The results are shown in Table 8, and the XRPD overlay is shown in FIG. 7.

TABLE 8

| Condition | | Time | Solid Form | Purity |
|---|---|---|---|---|
| Initial | — | — | Form CSV | 99.96% |
| 25° C./60% RH | Open | 6 months | Form CSV | 99.96% |
| 40° C./75% RH | Sealed | 6 months | Form CSV | 99.96% |
| | Open | | Form CSV | 99.96% |
| 60° C./75% RH | Sealed | 2 months | Form CSV | 99.94% |
| | Open | | Form CSV | 99.94% |

The results show that Form CSV is stable for at least 6 months at 25° C./60% RH and 40° C./75% RH. It indicates that Form CSV has good stability under both long-term and accelerated conditions. Form CSV is stable for at least 2 months at 60° C./75% RH. It indicates that Form CSV has good stability under stress conditions.

Example 8 Grinding Stability of Form CSV

Figure 8:
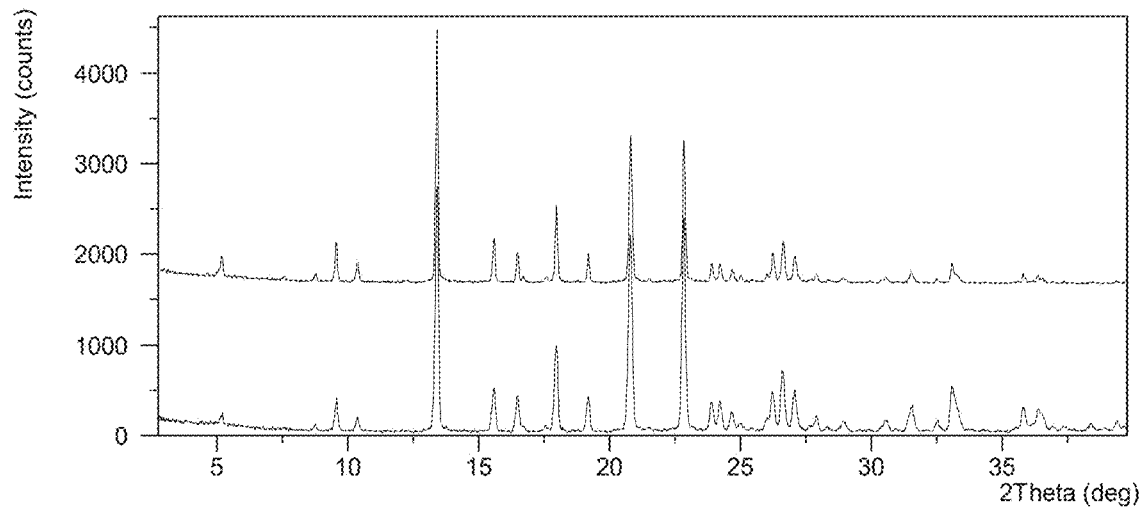
FIG. 8 shows an XRPD pattern overlay of Form CSV before and after grinding (top: after grinding, bottom: before grinding).
Figure 9:
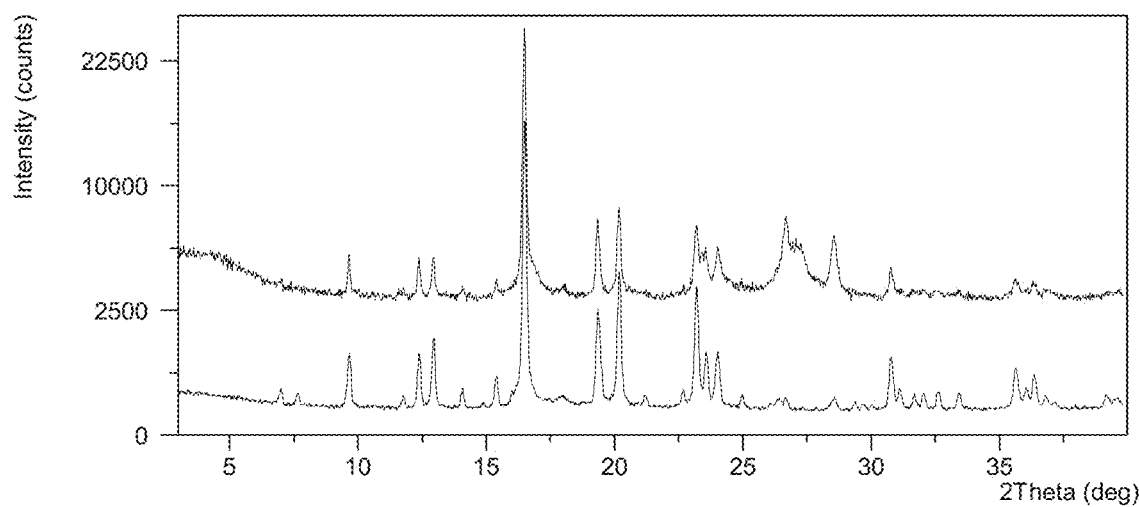
FIG. 9 shows an XRPD pattern overlay of WO2016038500 Form 1 before and after grinding (top: after grinding, bottom: before grinding).

A certain amount of Form CSV and WO2016038500 Form 1 were manually ground in the mortar for five minutes. The XRPD patterns before and after grinding were collected and shown in FIG. 8 and FIG. 9.

The results show that the crystallinity of Form CSV keeps substantially unchanged after grinding while the crystallinity of WO2016038500 Form 1 decreases. Compared with WO2016038500 Form 1, Form CSV has better mechanical stability.

Example 9 Compressibility of Form CSV

An ENERPAC manual tablet press was used for tableting. 80 mg of Form CSV and WO2016038500 Form 1 were weighed and added into the dies of a φ6 mm round tooling, compressed at 10 KN manually, then stored at room temperature for 24 hours until complete elastic recovery. Diameter (D) and thickness (L) were tested with a caliper. Hardness (H) was tested with an intelligent tablet hardness tester. Tensile strength of the powder was calculated with the following formula: $T=2H/\pi DL*9.8$. Under a certain force, the greater the tensile strength, the better the compressibility. The results are presented in Table 9.

TABLE 9

| Solid Form | Thickness (mm) | Diameter (mm) | Hardness (kgf) | Tensile strength (MPa) |
| --- | --- | --- | --- | --- |
| WO2016038500 Form 1 | 1.35 | 6.02 | 2.32 | 1.78 |
| Form CSV | 1.76 | 6.01 | 4.85 | 2.86 |

The results indicate that Form CSV has better compressibility compared with WO2016038500 Form 1.

Example 10 Hygroscopicity of Form CSV

Figure 10:
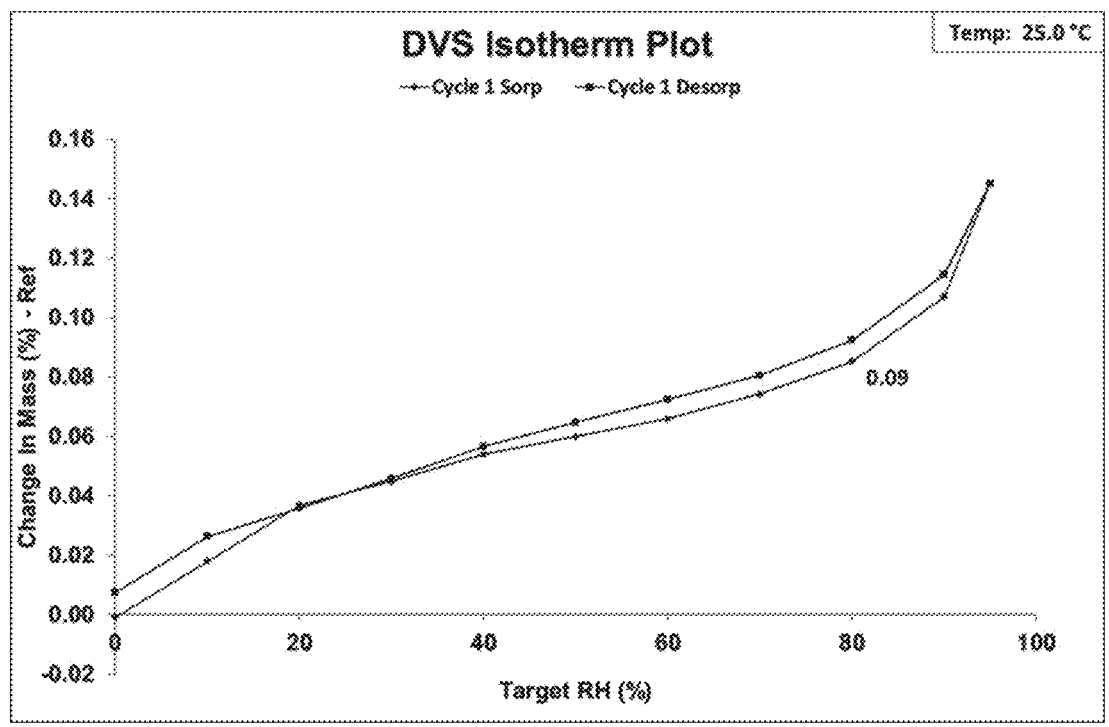
FIG. 10 shows a DVS plot of Form CSV.
Figure 11:
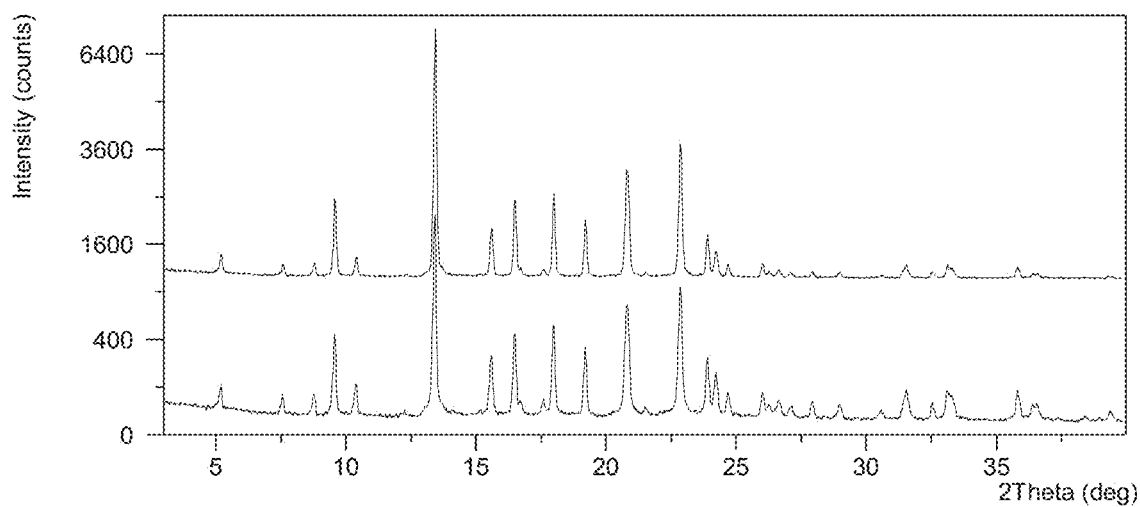
FIG. 11 shows an XRPD pattern overlay of Form CSV before and after DVS test (top: before DVS, bottom: after DVS).

Dynamic vapor sorption (DVS) was applied to test hygroscopicity of Form CSV with about 10 mg of sample. The weight gains at each relative humidity were recorded in a cycle of 0-95%-0 RH. The results are shown in FIG. 10. The XRPD patterns were collected before and after the DVS test and depicted in FIG. 11. Weight gain of Form CSV under 80% RH is 0.09%. Form CSV is non hygroscopic or almost non-hygroscopic.

Description and definition of hygroscopicity (general notice 9103 drug hygroscopicity test guidelines in 2015 edition of Chinese Pharmacopoeia, test at 25° C.+/−1° C., 80% RH. The definition of hygroscopicity in the 9th European Pharmacopoeia 5.11 is in consistent with the Chinese Pharmacopoeia.).

deliquescent: sufficient water is absorbed to form a solution.
  very hygroscopic: increase in mass is equal to or greater than 15 percent.
  hygroscopic: increase in mass is less than 15 percent and equal to or greater than 2 percent.
  slightly hygroscopic: increase in mass is less than 2 percent and equal to or greater than 0.2 percent.
  non hygroscopic or almost non hygroscopic: Increase in mass is less than 0.2%.

Example 11 Stability of Form CSV in Drug Product

Figure 12:
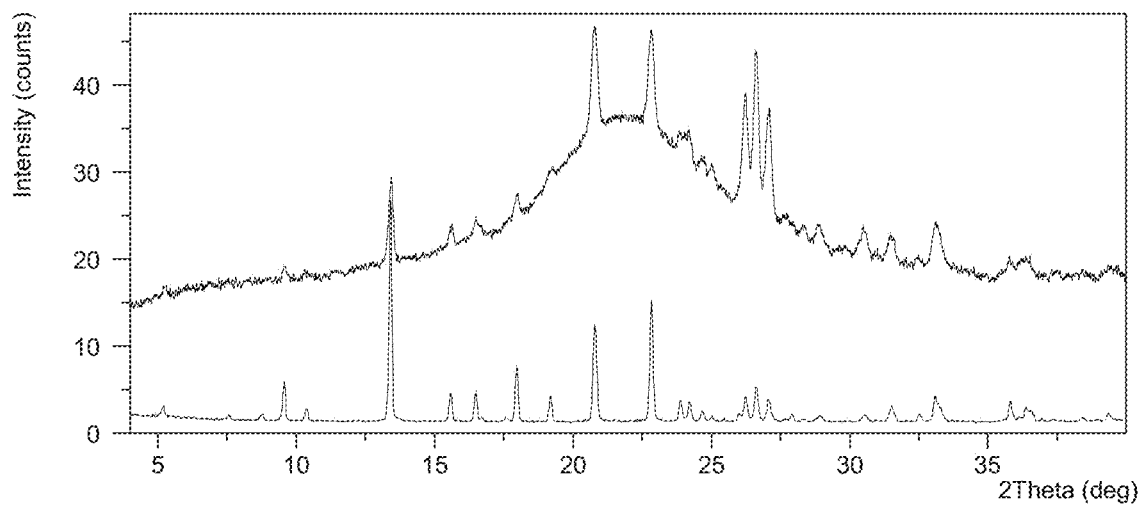
FIG. 12 shows an XRPD pattern overlay of Form CSV before and after production process (top: Form CSV drug product, bottom: Form CSV).

Form CSV drug products were prepared according to the formulation in Table 10 and the preparation process in Table 11. The XRPD patterns were collected before and after the formulation process. The XRPD overlay is shown in FIG. 12. The results indicate that Form CSV is stable in the formulation process.

TABLE 10

| No. | Component | mg/unit | % (w/w) | Function |
| --- | --- | --- | --- | --- |
| 1 | Form CSV | 72.5 | 11.93 | API |
| 2 | PEG 400 | 398.4 | 65.57 | Diluent |
| 3 | Fumaric acid | 16.1 | 2.65 | Stabilizer |
| 4 | Povidone (PVP K30) | 20.0 | 3.29 | Suspending agent |
| 5 | Dibutylhydroxytoluene (BHT) | 0.6 | 0.10 | Antioxidant |
| 6 | Polysorbate (Tween 80) | 100.0 | 16.46 | Surfactant |
| | Total | 607.6 | 100.0 | / |

Note:
72.5 mg of Form CSV is equivalent to 61 mg of Compound I.

TABLE 11

| Stage | Procedure |
| --- | --- |
| Inner fill preparation | Component of No. 2 and No. 3 were weighed into a glass vial according to the formulation, and the suspension was stirred at 40° C. about two minutes until a clear solution was obtained. Component No. 6 was added into the previously obtained solution and mixed homogeneously at room temperature. Component No. 4 and No. 5 were added into the previously obtained solution and mixed uniformly using ultrasonication. Component No. 1 was added into the previously obtained solution and the suspension was mixed uniformly via stirring. |
| Stability sample preparation | The ratio of the inner fill and the capsule fragments is 3:2 (w/w). 303 mg of the inner fill suspension and 202 mg of capsule fragments were added and mixed in the double aluminum blister. |

Figure 13:
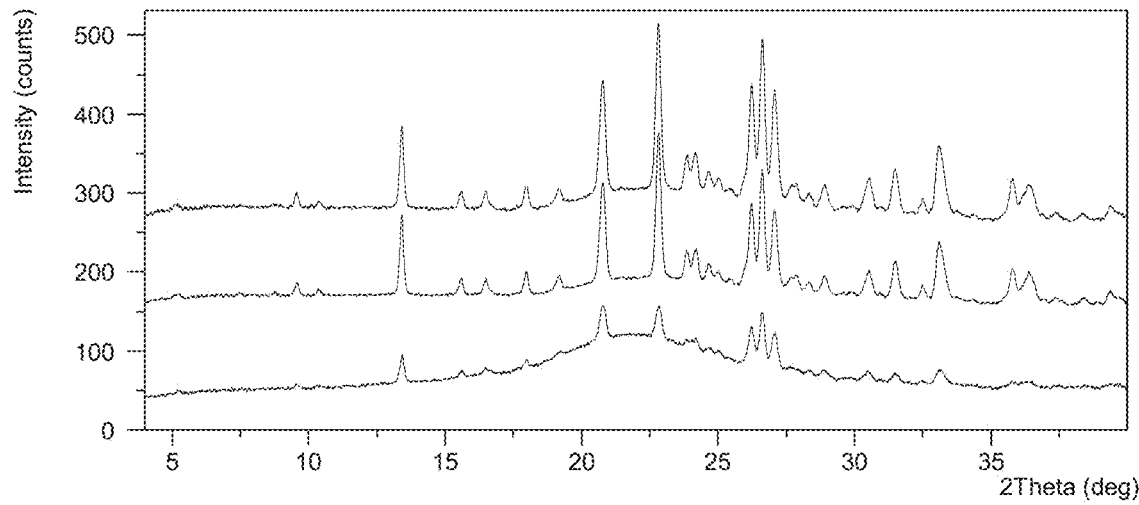
FIG. 13 shows an XRPD pattern overlay of Form CSV drug product (from top to bottom: stored in double aluminum blister under 25° C./60% RH for three months, stored in double aluminum blister under 40° C./75% RH for three months, initial drug product).

The stability results are shown in Table 12 and the XRPD overlay is shown in FIG. 13. The results show that Form CSV in drug product is stable for at least 3 months at 25° C./60% RH and 40° C./75% RH conditions.

TABLE 12

| Condition | Time | Solid Form | Purity % |
| --- | --- | --- | --- |
| Initial | — | Form CSV | 99.84 |
| 25° C./60% RH | 3 months | Form CSV | 99.87 |
| 40° C./75% RH | 3 months | Form CSV | 99.86 |

Example 12 Dissolution Profile of Form CSV Drug Product

Figure 14:
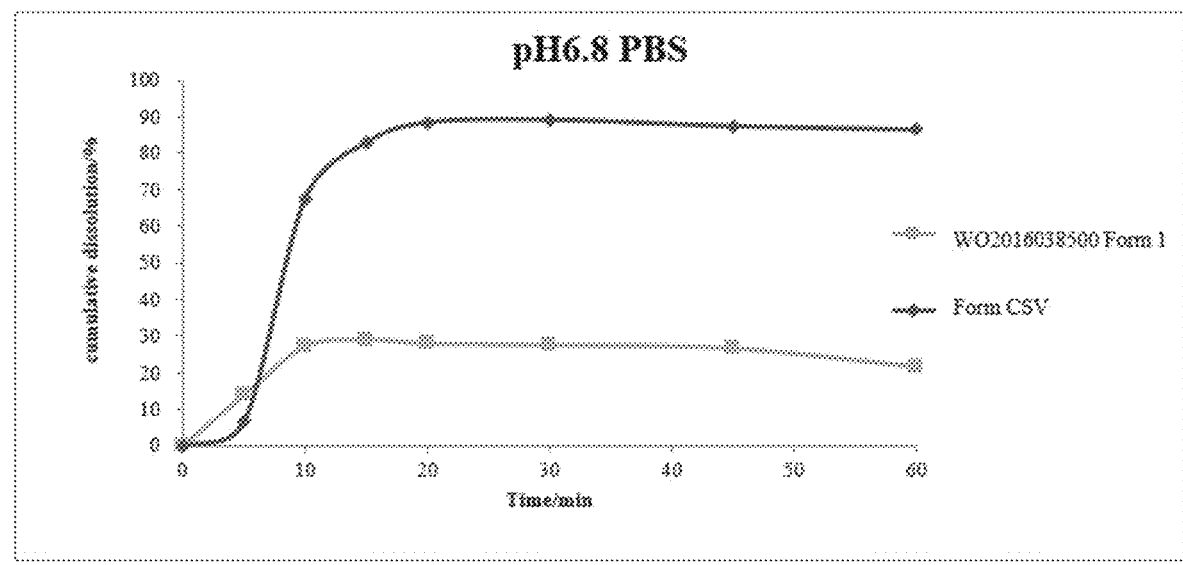
FIG. 14 shows a dissolution curve of Form CSV drug product and WO2016038500 Form 1 drug product in pH6.8 PBS.

Form CSV and WO2016038500 Form 1 were made into capsules according to formulation and preparation process in Table 13 and Table 14. The cumulative dissolution was measured at different time in pH6.8 PBS. The dissolution conditions are listed in Table 15. The dissolution results are presented in Table 16 and FIG. 14.

TABLE 13

| No. | Component | mg/unit | % (w/w) | Function |
|---|---|---|---|---|
| 1 | Form CSV | 72.5 | 12.08 | API |
| 2 | PEG 400 | 390.8 | 65.13 | Diluent |
| 3 | Fumaric acid | 16.1 | 2.68 | Stabilizer |
| 4 | Povidone (PVP K30) | 20.0 | 3.33 | Suspending agent |
| 5 | Dibutylhydroxytoluene (BHT) | 0.6 | 0.10 | Antioxidant |
| 6 | Polysorbate (Tween 80) | 100.0 | 16.67 | Surfactant |
|   | Total | 600.0 | 100.0 | / |

Note:
72.5 mg of Form CSV is equivalent to 61 mg of Compound I. 600 mg of inner fill were added into 0# gelatin capsule and the capsule was sealed.

TABLE 14

| No. | Component | mg/unit | % (w/w) | Function |
|---|---|---|---|---|
| 1 | WO2016038500 Form 1 | 61 | 10.17 | API |
| 2 | PEG 400 | 402.3 | 67.05 | Diluent |
| 3 | Fumaric acid | 16.1 | 2.68 | Stabilizer |
| 4 | Povidone (PVP K30) | 20.0 | 3.33 | Suspending agent |
| 5 | Dibutylhydroxytoluene (BHT) | 0.6 | 0.10 | Antioxidant |
| 6 | Polysorbate (Tween 80) | 100.0 | 16.67 | Surfactant |
|   | Total | 600.0 | 100.0 | / |

600 mg of inner fill were added into 0# gelatin capsule and the capsule was sealed.

TABLE 15

| | |
|---|---|
| Equipment | Sotax AT7 |
| Method | Paddle |
| Dose | 61 mg |
| Volume | 900 mL |
| Speed | 50 rpm |
| Temperature | 37° C. |
| Sampling point | pH 6.8 PBS: 5, 10, 15, 20, 30, 45, 60 min |
| Media replenishment | No |

TABLE 16

| Time (min) | Cumulative drug release (%) | |
|---|---|---|
| | WO2016038500 Form 1 | Form CSV |
| 0 | 0.0 | 0.0 |
| 5 | 14.0 | 6.6 |
| 10 | 27.3 | 67.6 |
| 15 | 29.1 | 82.8 |
| 20 | 28.1 | 88.4 |
| 30 | 27.6 | 89.1 |
| 45 | 26.8 | 87.4 |
| 60 | 21.8 | 86.4 |

Form CSV shows higher cumulative drug release than WO2016038500 Form 1 in pH6.8 PBS. Compared with WO2016038500 Form 1, Form CSV has better bioavailability.

Example 13 Preparation of Form CSVI 15.4 mg of tafamidis free acid and 19.3 mg of glutaric acid were weighed into a 1.5-mL glass vial. 1.0 mL of ethyl acetate was added. The suspension was stirred at room temperature for about seven days. A crystalline solid was obtained by separation.

Figure 15:
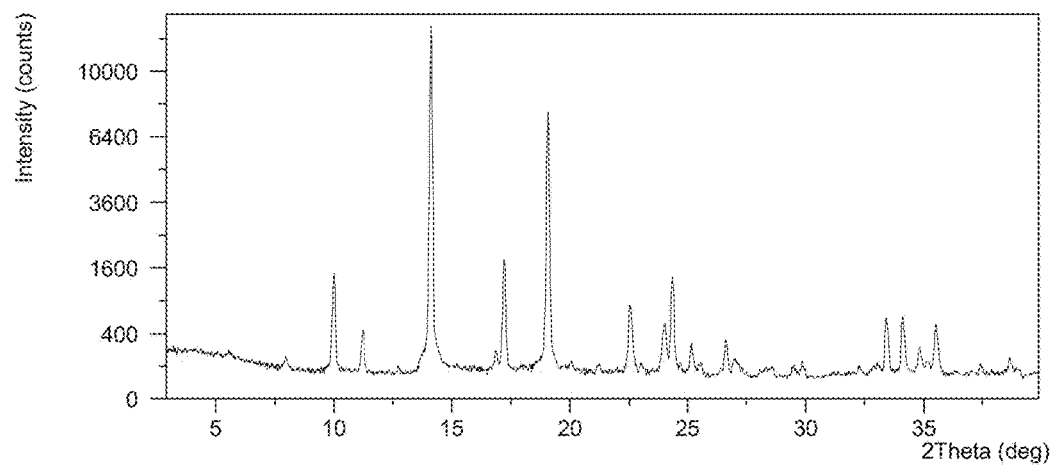
FIG. 15 shows an XRPD pattern of Form CSVI in Example 13.

The obtained solid was confirmed to be Form CSVI by XRPD. The XRPD pattern is substantially as depicted in FIG. 15, and the XRPD data are listed in Table 17.

TABLE 17

| 2θ | d spacing | Intensity % |
|---|---|---|
| 9.98 | 8.87 | 10.74 |
| 11.21 | 7.89 | 2.94 |
| 14.11 | 6.28 | 100.00 |
| 16.85 | 5.26 | 1.27 |
| 17.20 | 5.15 | 13.63 |
| 19.05 | 4.66 | 58.71 |
| 22.53 | 3.95 | 5.72 |
| 24.01 | 3.71 | 3.86 |
| 24.34 | 3.66 | 10.38 |
| 25.15 | 3.54 | 1.77 |
| 26.60 | 3.35 | 2.18 |
| 33.39 | 2.68 | 4.32 |
| 34.08 | 2.63 | 4.59 |
| 34.80 | 2.58 | 1.48 |
| 35.49 | 2.53 | 3.67 |

Figure 16:
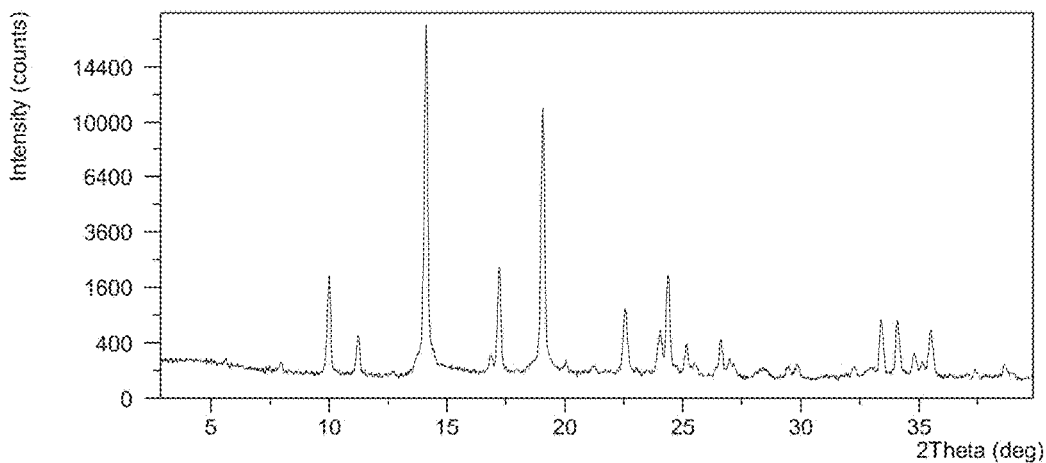
FIG. 16 shows an XRPD pattern of Form CSVI in Example 14.

Example 14 Preparation of Form CSVI 454.3 mg of tafamidis free acid and 597.7 mg of glutaric acid were weighed into a 20-mL glass vial. 10.0 mL of ethyl acetate was added. After stirred at room temperature for about six days, a solid was obtained by separation and vacuum drying at 30° C. for about 2.5 hours. The solid was stirred in 10.0 mL of ethyl acetate at room temperature for about two days. Then, 134.4 mg of glutaric acid was added and further stirred for 4 days. The solid was separated and vacuum dried at 25° C. overnight. The solid was suspended in 20.0 mL of n-heptane and stirred at room temperature for 1 day. The obtained solid by separation was vacuum dried at 25° C. overnight. 20.5 mg of the dry solid was weighed into a 1.5-mL glass vial and 1.0 mL of n-heptane/ethyl acetate (4:1, v/v) was added. The suspension was stirred at room temperature overnight. A crystalline solid was obtained by separation. The obtained solid was confirmed to be Form CSVI by XRPD. The XRPD pattern is substantially as depicted in FIG. 16, and the XRPD data are listed in Table 18.

Figure 17:
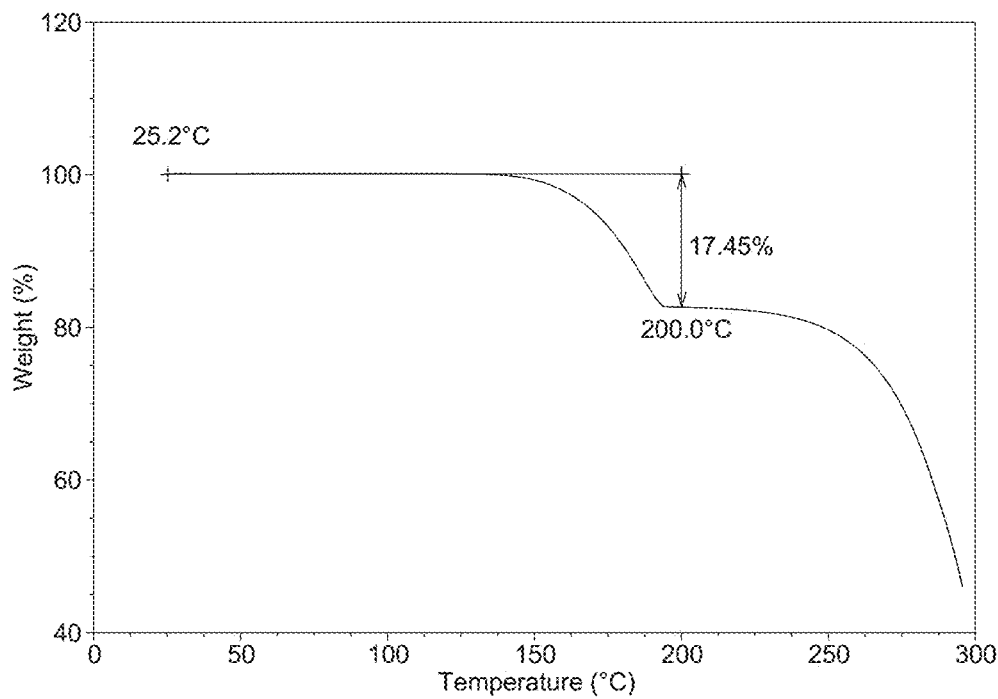
FIG. 17 shows a TGA curve of Form CSVI in Example 14.

The TGA curve of Form CSVI is substantially as depicted in FIG. 17, which shows about 17.5% weight loss when heated to 200° C., corresponding to the loss of glutaric acid.

Figure 18:
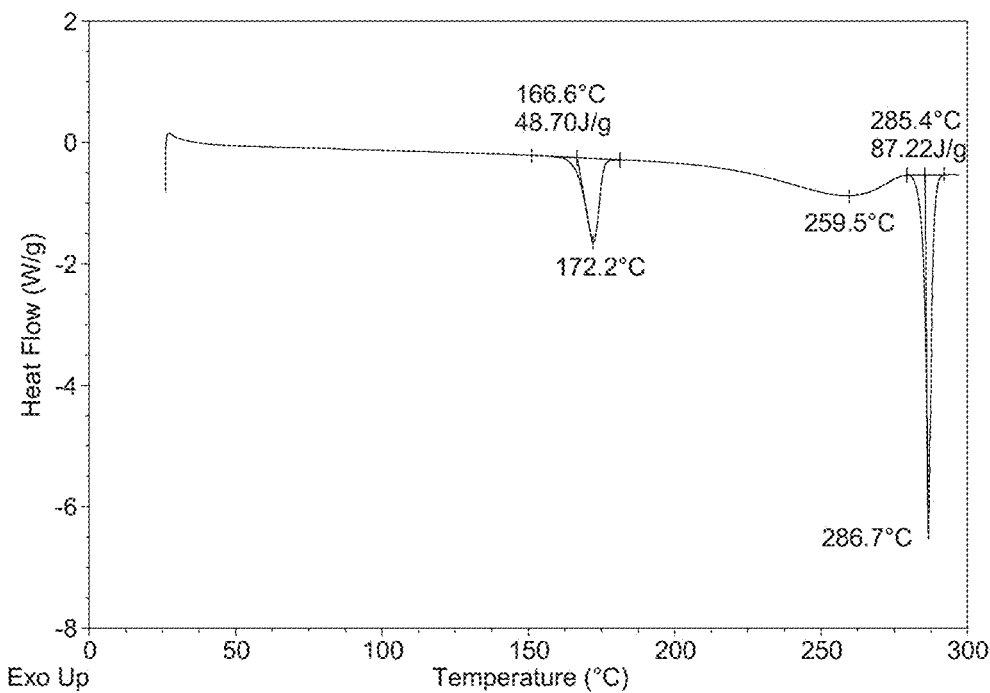
FIG. 18 shows a DSC curve of Form CSVI in Example 14.

The DSC curve of Form CSVI is substantially as depicted in FIG. 18, which shows one endothermic peak at around 166.6° C. (onset temperature).

Figure 19:
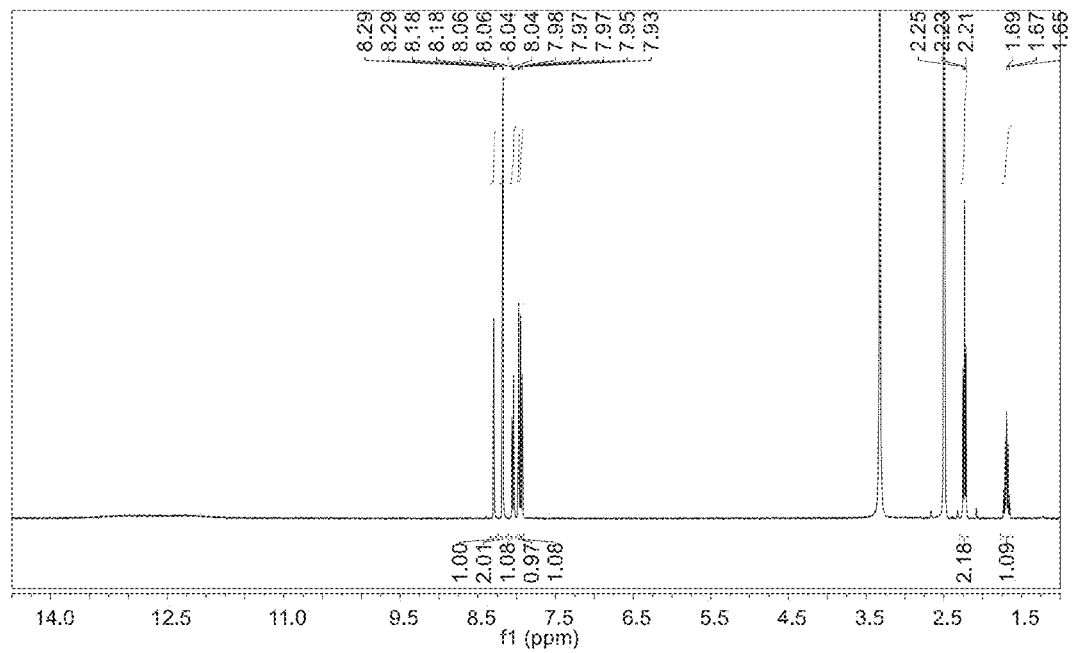
FIG. 19 shows a $^1$H NMR spectrum of Form CSVI in Example 14.

The $^1$H NMR spectrum of Form CSVI is substantially as depicted in FIG. 19, which complies with Compound I. The chemical shifts at δ=2.23 and 1.69 are the characteristic peaks of glutaric acid. The $^1$H NMR spectrum indicates that in Form CSVI, the molar ratio of tafamidis and glutaric acid equals 1:0.5. The corresponding data are: $^1$H NMR (400 MHz, DMSO) δ 8.29 (d, J=0.9 Hz, 1H), 8.18 (d, J=1.9 Hz, 2H), 8.05 (dd, J=8.4, 1.4 Hz, 1H), 7.97 (t, J=1.9 Hz, 1H), 7.94 (d, J=8.3 Hz, 1H), 2.23 (t, J=7.4 Hz, 2H), 1.69 (p, J=7.4 Hz, 1H).

TABLE 18

| 2θ | d spacing | Intensity % |
|---|---|---|
| 9.98 | 8.86 | 10.57 |
| 11.21 | 7.90 | 2.35 |
| 14.11 | 6.28 | 100.00 |

TABLE 18-continued

| 2θ | d spacing | Intensity % |
|---|---|---|
| 16.85 | 5.26 | 1.10 |
| 17.20 | 5.16 | 11.98 |
| 19.05 | 4.66 | 60.47 |
| 22.53 | 3.95 | 5.47 |
| 24.01 | 3.71 | 3.05 |
| 24.34 | 3.66 | 10.77 |
| 25.14 | 3.54 | 1.84 |
| 26.60 | 3.35 | 2.23 |
| 33.38 | 2.68 | 4.13 |
| 34.07 | 2.63 | 4.15 |
| 34.78 | 2.58 | 1.20 |
| 35.47 | 2.53 | 2.97 |

Example 15 Kinetic Solubility of Form CSVI

When solubility test is used to forecast the in vivo performance of a drug, it is critical that the in vitro test mimics the conditions in vivo as closely as possible.
20 mg of Form CSVI and 20 mg of WO2016038500 Form 1 were suspended into 3.0 mL of SGF to get saturated solutions. After equilibrated for one hour, concentrations (μg/mL) of compound I in the saturated solutions were measured by UPLC. The results are listed in Table 19.

TABLE 19

| Medium | Form CSVI | WO2016038500 Form 1 |
|---|---|---|
| SGF | 2.4 | 1.5 |

The results show that the solubility of Form CSVI in SGF is higher than that of WO2016038500 Form 1.

Example 16 Stability of Form CSVI

Figure 20:
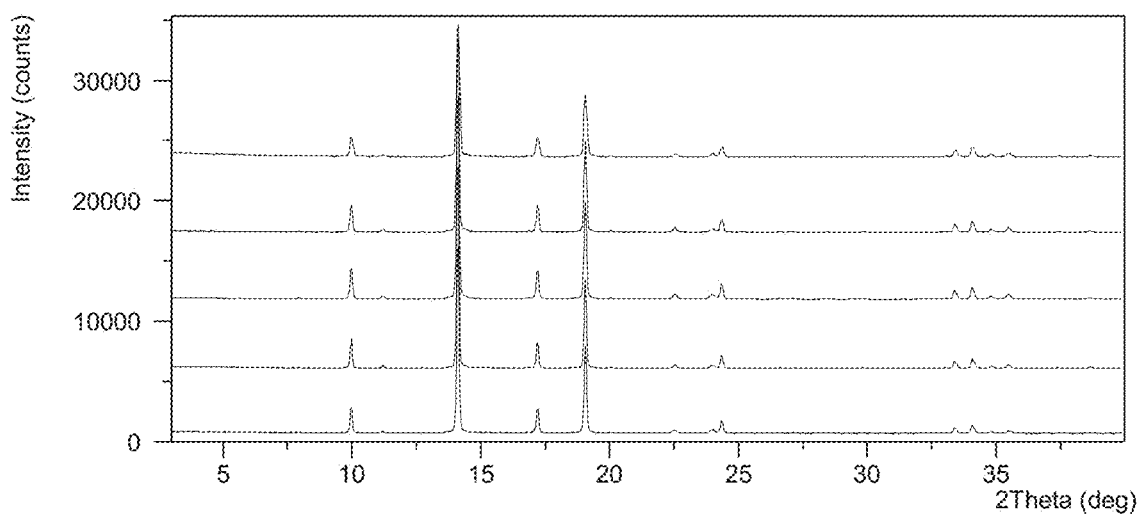
FIG. 20 shows an XRPD pattern overlay of Form CSVI of the present disclosure before and after storage (from top to bottom: stored at 60° C./75% RH (sealed) for two months, stored at 40° C./75% RH (open) for six months, stored at 40° C./75% RH (sealed) for six months, stored at 25° C./60% RH (open) for six months, initial).

Approximately 5 mg of solid samples of Form CSVI were stored under different conditions of 25° C./60% RH, 40° C./75% RH and 60° C./75% RH. Crystalline form and purity were checked by XRPD and HPLC, respectively. The results are shown in Table 20, and the XRPD overlay is shown in FIG. 20.

TABLE 20

| Condition | | Time | Solid Form | Purity |
|---|---|---|---|---|
| Initial | | — | Form CSVI | 99.95% |
| 25° C./60% RH | Open | 6 months | Form CSVI | 99.96% |
| 40° C./75% RH | Sealed | 6 months | Form CSVI | 99.95% |
| | Open | | Form CSVI | 99.95% |
| 60° C./75% RH | Sealed | 2 months | Form CSVI | 99.95% |

The results show that Form CSVI is stable for at least 6 months at 25° C./60% RH and 40° C./75% RH. It shows that Form CSVI has good stability under both long-term and accelerated conditions. Form CSVI is stable for at least 2 months at 60° C./75% RH. It shows that CSVI has good stability under stress conditions.

Example 17 Hygroscopicity of Form CSVI

Figure 21:
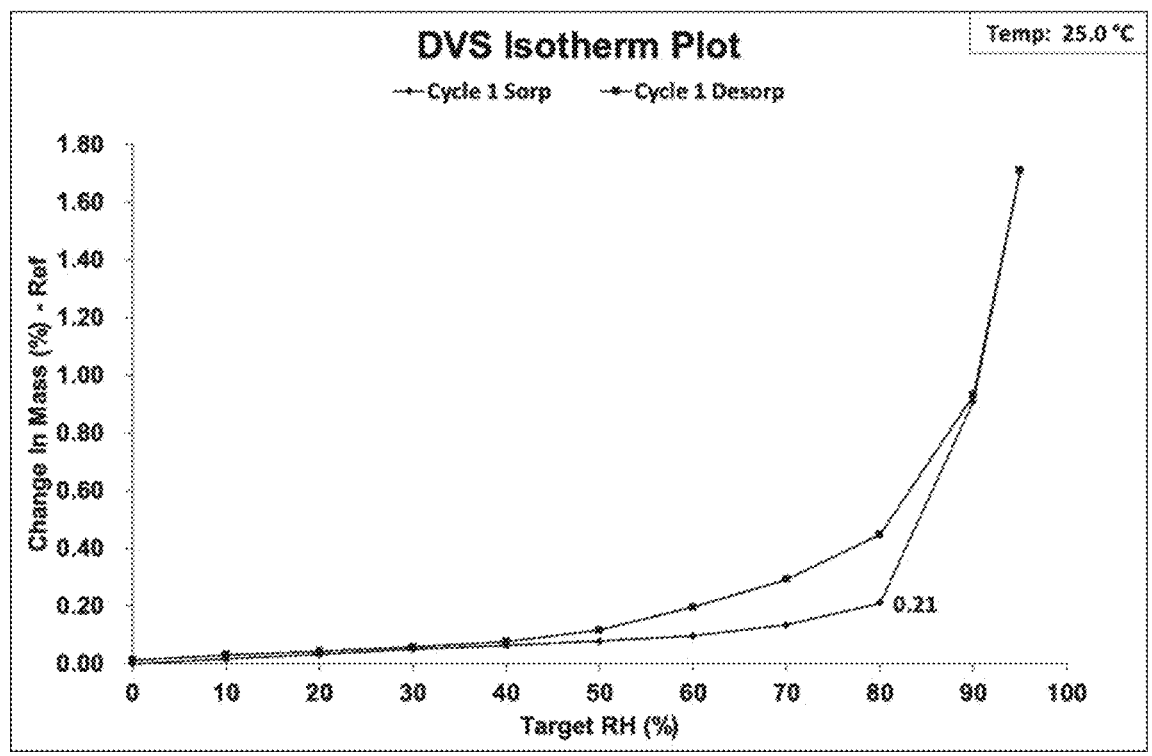
FIG. 21 shows a DVS plot of Form CSVI.
Figure 22:
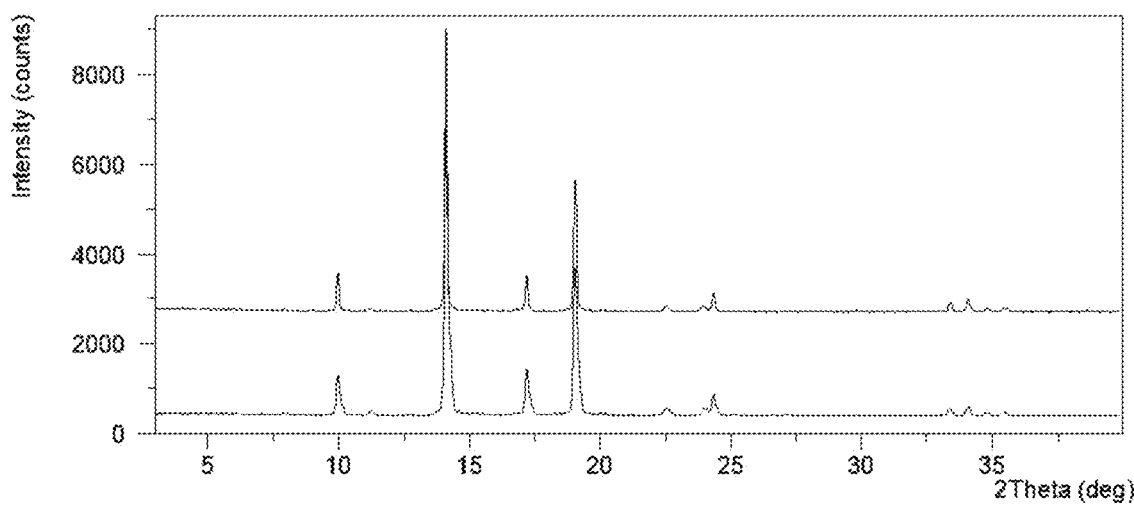
FIG. 22 shows an XRPD pattern overlay of Form CSVI before and after DVS test (top: before DVS, bottom: after DVS).

Dynamic vapor sorption (DVS) was applied to test hygroscopicity of Form CSVI with about 10 mg of samples. The weight gains at each relative humidity were recorded in a cycle of 0-95%-0RH. The results are shown in FIG. 21. The XRPD patterns were collected before and after the DVS test and depicted in FIG. 22. Weight gain of Form CSVI under 80% RH is 0.21%. Form CSVI is slightly hygroscopic.

Example 18 Dissolution Profile of Form CSVI Drug Product

Figure 23:
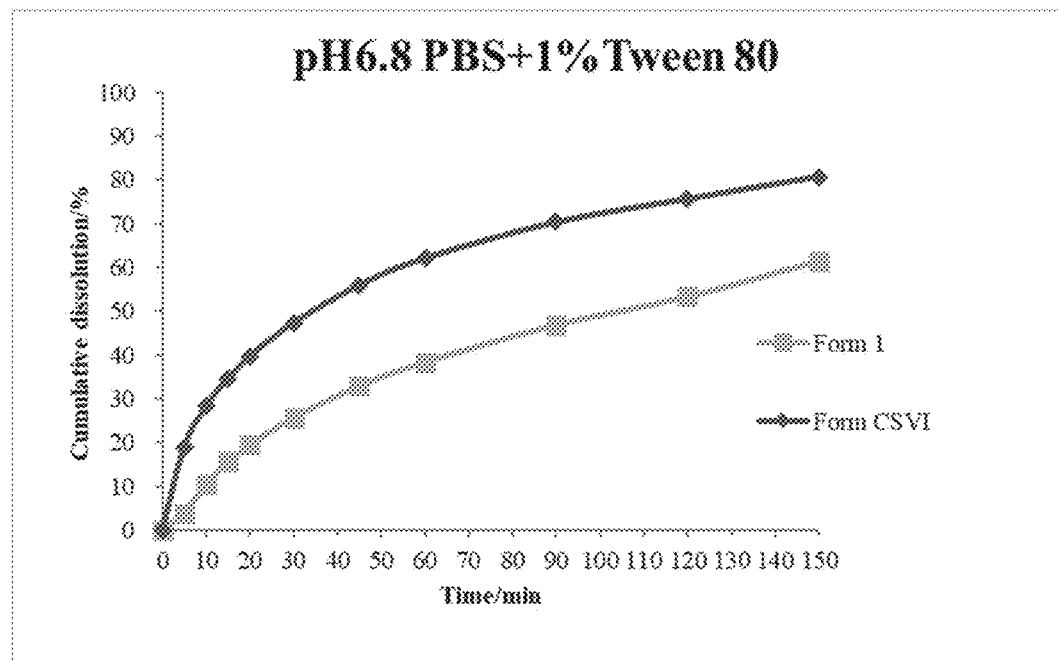
FIG. 23 shows a dissolution curve of Form CSVI drug product and WO2016038500 Form 1 drug product in pH6.8 PBS+1% Tween 80.
Figure 24:
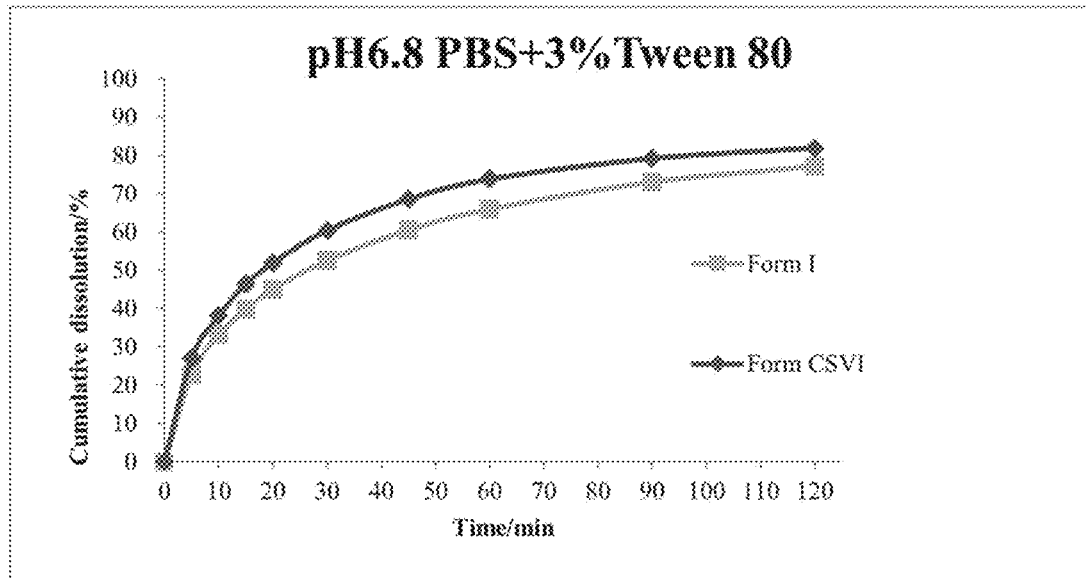
FIG. 24 shows a dissolution curve of Form CSVI drug product and WO2016038500 Form 1 drug product in pH6.8 PBS+3% Tween 80.

Form CSVI and WO2016038500 Form 1 were made into tablets according to formulation and preparation process in Table 21. The cumulative dissolution was measured at different time in pH6.8 PBS+1% Tween 80 and pH6.8 PBS+3% Tween 80. The dissolution conditions are listed in Table 22 and Table 23. The dissolution results are presented in Table 24 (FIG. 23) and Table 25 (FIG. 24).

TABLE 21

| No. | Component | Form CSVI mg/unit | Form CSVI % (w/w) | WO2016038500 Form 1 mg/unit | WO2016038500 Form 1 % (w/w) | Function |
|---|---|---|---|---|---|---|
| | | Intra-granular | | | | |
| 1 | Crystalline API | 74.1 | 37.050 | 61.00 | 30.500 | API |
| 2 | Microcrystalline cellulose | 122.4 | 61.200 | 135.50 | 67.750 | Diluent |
| 3 | Crosslinked povidone | 2.0 | 1.000 | 2.0 | 1.000 | Disintegrant |
| 4 | Magnesium stearate | 0.25 | 0.125 | 0.25 | 0.125 | Lubricant |
| | | Extra-granular | | | | |
| 5 | Crosslinked povidone | 1.0 | 0.500 | 1.0 | 0.500 | Disintegrant |
| 6 | Magnesium stearate | 0.25 | 0.125 | 0.25 | 0.125 | Lubricant |
| | Total | 200.0 | 100.000 | 200.0 | 100.000 | / |

Note:
74.1 mg of Form CSVI is equivalent to 61 mg of Compound I.

TABLE 22

| Equipment | Sotax AT7 |
|---|---|
| Method | Paddle |
| Dose | 61 mg |
| Volume | 900 mL |
| Speed | 75 rpm |
| Temperature | 37° C. |
| Sampling point | pH 6.8 PBS + 1% Tween 80: 5, 10, 15, 20, 30, 45, 60, 90, 120, 150 min |
| Media replenishment | No |

TABLE 23

| Equipment | Sotax AT7 |
|---|---|
| Method | Paddle |
| Dose | 61 mg |
| Volume | 900 mL |
| Speed | 75 rpm |
| Temperature | 37° C. |
| Sampling point | pH 6.8 PBS + 3% Tween 80: 5, 10, 15, 20, 30, 45, 60, 90, 120 min |
| Media replenishment | No |

TABLE 24

| Time (min) | Cumulative drug release in pH 6.8 PBS + 1% Tween 80 (%) | |
| --- | --- | --- |
| | WO2016038500 Form 1 | Form CSVI |
| 0 | 0.0 | 0.0 |
| 5 | 4.0 | 19.1 |
| 10 | 10.4 | 28.3 |
| 15 | 15.6 | 34.7 |
| 20 | 19.5 | 39.8 |
| 30 | 25.7 | 47.4 |
| 45 | 33.0 | 56.0 |
| 60 | 38.4 | 62.1 |
| 90 | 46.8 | 70.4 |
| 120 | 53.3 | 75.7 |
| 150 | 61.4 | 80.7 |

TABLE 25

| Time (min) | Cumulative drug release in pH 6.8 PBS + 3% Tween 80 (%) | |
| --- | --- | --- |
| | WO2016038500 Form 1 | Form CSVI |
| 0 | 0.0 | 0.0 |
| 5 | 22.7 | 27.0 |
| 10 | 33.1 | 38.2 |
| 15 | 39.7 | 46.4 |
| 20 | 45.0 | 51.9 |
| 30 | 52.5 | 60.4 |
| 45 | 60.5 | 68.5 |
| 60 | 65.9 | 73.8 |
| 90 | 73.0 | 79.2 |
| 120 | 77.2 | 81.9 |

Form CSVI shows higher cumulative drug release than that of WO2016038500 Form 1 in pH6.8 PBS+1% Tween 80 and pH6.8 PBS+3% Tween 80. Compared with WO2016038500 Form 1, Form CSVI has better bioavailability.

Example 19 Preparation of Form CSVII 308.9 mg of tafamidis free acid and 145.9 mg of adipic acid were weighed into a 20-mL glass vial. 15 mL of ethyl acetate was added. After stirring at 50° C. for about five days, another 72.9 mg of adipic acid was added. After stirring at 50° C. for about two days, another 29.1 mg of adipic acid was added. After stirred at 50° C. for about six days, the suspension was suction filtered. The solid was dried with forced air convection at 25° C. for about 4.5 hours. The dry solid was stirred in 10 mL of acetone/n-heptane (1:4, v/v) at room temperature overnight. The suspension was suction filtered and the obtained solid was vacuum dried at 30° C. overnight. A crystalline solid was obtained.

Figure 25:
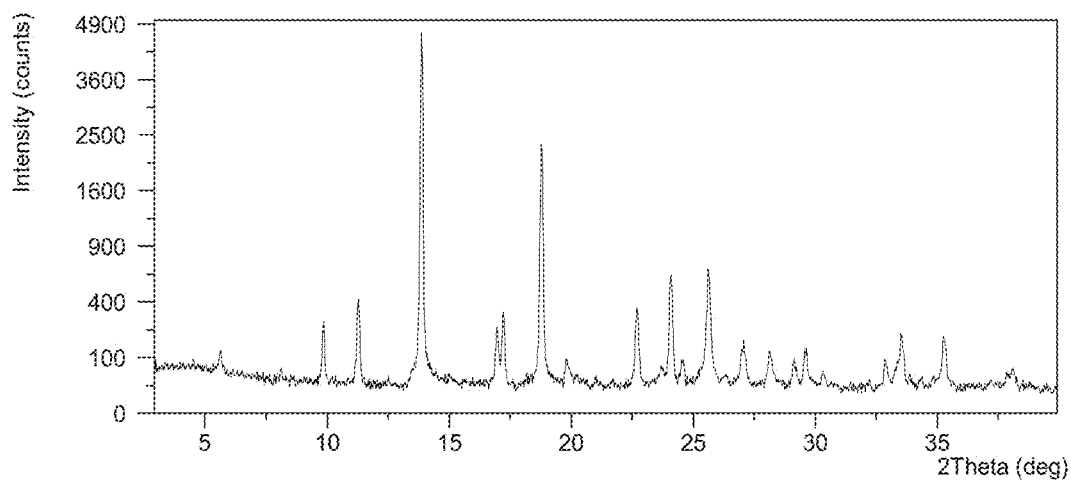
FIG. 25 shows an XRPD pattern of Form CSVII in Example 19.

The obtained solid was confirmed to be Form CSVII by XRPD. The XRPD pattern is substantially as depicted in FIG. 25, and the XRPD data are listed in Table 26.

Figure 26:
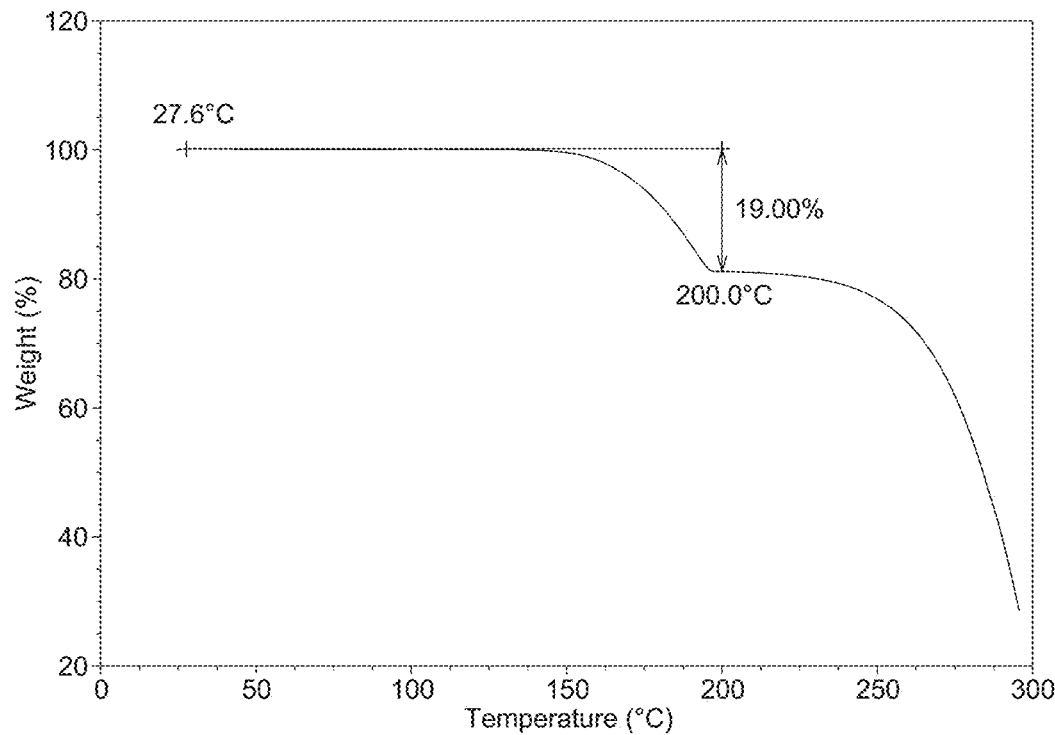
FIG. 26 shows a TGA curve of Form CSVII in Example 19.
Figure 27:
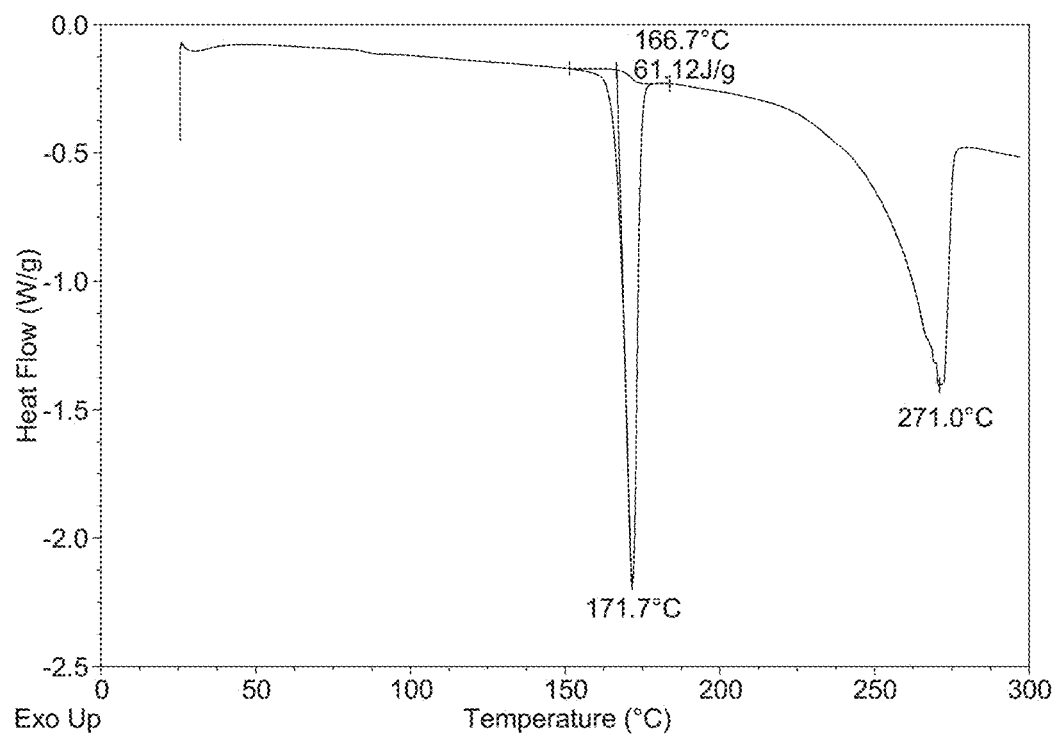
FIG. 27 shows a DSC curve of Form CSVII in Example 19.

The TGA curve of Form CSVII is substantially as depicted in FIG. 26, which shows about 19.0% weight loss when heated to 200° C., corresponding to the loss of adipic acid. The DSC curve of Form CSVII is substantially as depicted in FIG. 27, which shows one endothermic peak at around 166.7° C. (onset temperature).

Figure 28:
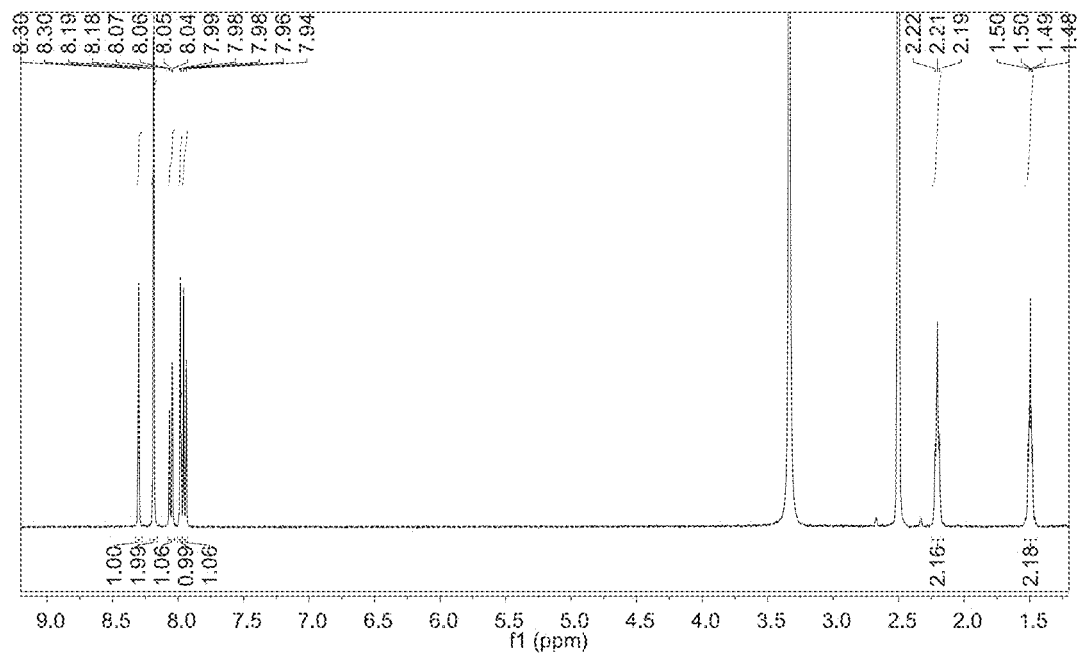
FIG. 28 shows a $^1$H NMR spectrum of Form CSVII in Example 19.

The $^1$H NMR spectrum of Form CSVII is substantially as depicted in FIG. 28, which complies with Compound I. The chemical shifts at δ=2.21 and 1.55-1.44 are the characteristic peaks of adipic acid. The $^1$H NMR spectrum indicates that in Form CSVII, the molar ratio of tafamidis and adipic acid equals 1:0.5. The corresponding data are: $^1$H NMR (400 MHz, DMSO) δ 8.30 (d, J=0.8 Hz, 1H), 8.19 (d, J=1.9 Hz, 2H), 8.05 (dd, J=8.4, 1.4 Hz, 1H), 7.98 (t, J=1.9 Hz, 1H), 7.95 (d, J=8.4 Hz, 1H), 2.21 (t, J=6.5 Hz, 2H), 1.55-1.44 (m, 2H).

TABLE 26

| 2θ | d spacing | Intensity % |
| --- | --- | --- |
| 5.61 | 15.77 | 1.51 |
| 9.84 | 8.99 | 5.11 |
| 11.27 | 7.85 | 8.33 |
| 13.86 | 6.39 | 100.00 |
| 16.95 | 5.23 | 4.56 |
| 17.20 | 5.15 | 6.48 |
| 18.77 | 4.73 | 49.82 |
| 19.79 | 4.49 | 1.40 |
| 22.67 | 3.92 | 7.21 |
| 24.07 | 3.70 | 12.72 |
| 24.55 | 3.63 | 1.53 |
| 25.61 | 3.48 | 13.83 |
| 27.03 | 3.30 | 2.78 |
| 28.13 | 3.17 | 2.01 |
| 29.12 | 3.07 | 1.45 |
| 29.59 | 3.02 | 2.10 |
| 32.84 | 2.73 | 1.51 |
| 33.51 | 2.67 | 3.98 |
| 35.25 | 2.55 | 3.66 |

Example 20 Kinetic Solubility of Form CSVII 20 mg of Form CSVII and 20 mg of WO2016038500 Form 1 were suspended into 3.0 mL of SGF, 3.0 mL of FaSSIF and 3.0 mL of FaSSIF to get saturated solutions. After equilibrated for one hour, concentrations (μg/mL) of compound I in the saturated solutions were measured by UPLC. The results are listed in Table 27.

TABLE 27

| Medium | Form CSVII | WO2016038500 Form 1 |
| --- | --- | --- |
| SGF | 19.4 | 1.5 |
| FeSSIF | 1.3 | 0.6 |
| FaSSIF | 13.3 | 9.0 |

The results show that the solubility of Form CSVII in SGF, FaSSIF and FeSSIF is higher than that of WO2016038500 Form 1 in the prior art. In particular, in SGF, the solubility of Form CSVII is 12 times than that of WO2016038500 Form 1.

Example 21 Stability of Form CSVII

Figure 29:
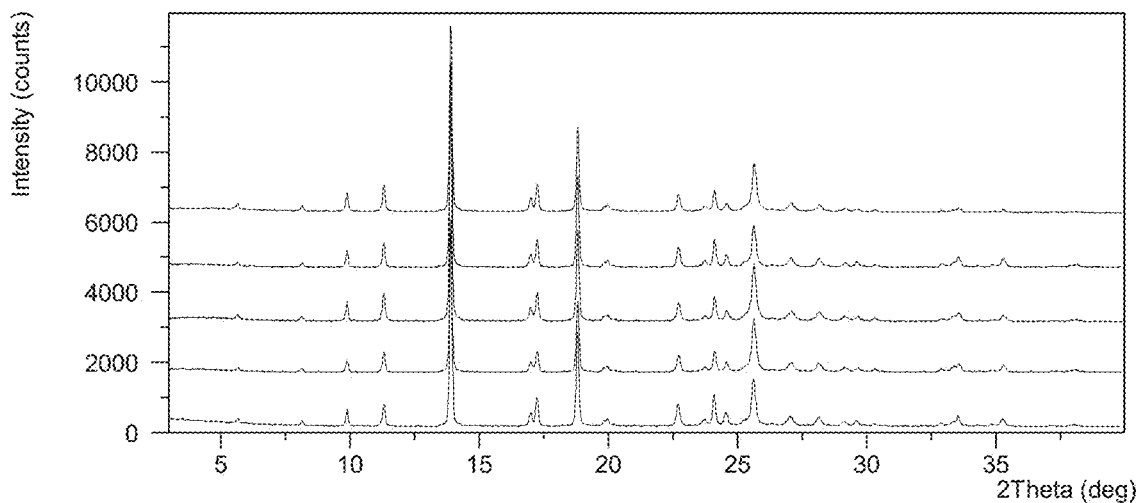
FIG. 29 shows an XRPD pattern overlay of Form CSVII of the present disclosure before and after storage (from top to bottom: stored at 60° C./75% RH (sealed) for two months, stored at 40° C./75% RH (open) for three months, stored at 40° C./75% RH (sealed) for three months, stored at 25° C./60% RH (open) for three months, initial).

Approximately 5 mg of solid samples of Form CSVII were stored under different conditions of 25° C./60% RH, 40° C./75% RH and 60° C./75% RH. Crystalline form and purity were checked by XRPD and HPLC, respectively. The results are shown in Table 28, and the XRPD overlay is shown in FIG. 29.

TABLE 28

| Condition | | Time | Solid Form | Purity |
|---|---|---|---|---|
| Initial | — | — | Form CSVII | 99.93% |
| 25° C./60% RH | Open | 3 months | Form CSVII | 99.92% |
| 40° C./75% RH | Sealed | 3 months | Form CSVII | 99.92% |
| | Open | | Form CSVII | 99.92% |
| 60° C./75% RH | Sealed | 2 months | Form CSVII | 99.93% |

The results show that Form CSVII is stable for at least 3 months at 25° C./60% RH and 40° C./75% RH. It indicates that Form CSVII has good stability under both long-term and accelerated conditions. Form CSVII is stable for at least 2 months at 60° C./75% RH. It indicates that Form CSVII has good stability under stress conditions.

Example 22 Compressibility of Form CSVII

An ENERPAC manual tablet press was used for tableting 80 mg of Form CSVII and WO2016038500 Form 1 were weighed and added into the dies of a φ6 mm round tooling, compressed at 10 KN manually, then stored at room temperature for 24 hours until complete elastic recovery. Diameter (D) and thickness (L) were tested with a caliper. Hardness (H) was tested with an intelligent tablet hardness tester. Tensile strength of the powder was calculated with the following formula: T=2H/πDL*9.8. Under a certain force, the greater the tensile strength, the better the compressibility. The results are presented in Table 29.

TABLE 29

| Solid Form | Thickness (mm) | Diameter (mm) | Hardness (kgf) | Tensile strength (MPa) |
|---|---|---|---|---|
| WO2016038500 Form 1 | 1.35 | 6.02 | 2.32 | 1.78 |
| Form CS VII | 1.93 | 6.00 | 7.45 | 4.02 |

The results indicate that Form CSVII has better compressibility compared with WO2016038500 Form 1.

Example 23 Hygroscopicity of Form CSVII

Figure 30:
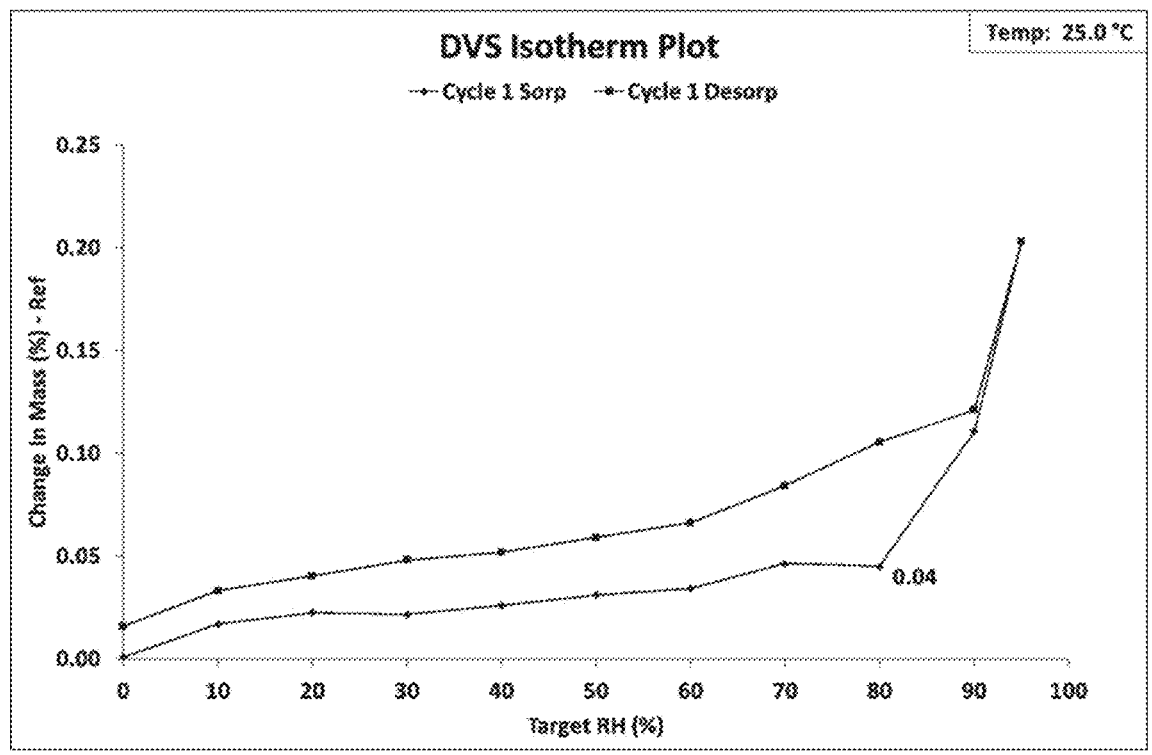
FIG. 30 shows a DVS plot of Form CSVII.
Figure 31:
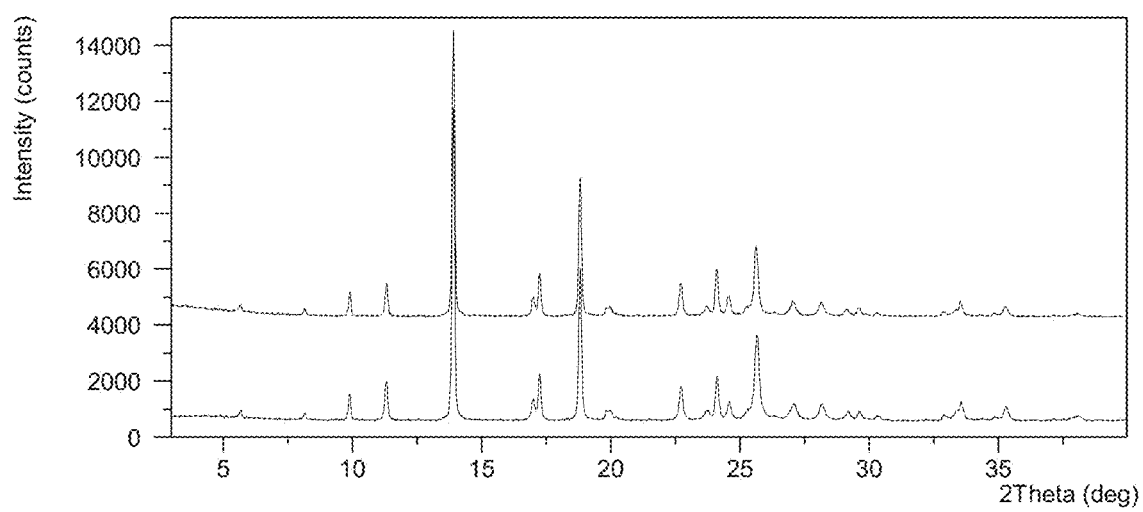
FIG. 31 shows an XRPD pattern overlay of Form CSVII before and after DVS test (top: before DVS, bottom: after DVS).

Dynamic vapor sorption (DVS) was applied to test hygroscopicity of Form CSVII with about 10 mg of samples. The weight gains at each relative humidity were recorded in a cycle of 0-95%-0RH. The results are shown in FIG. 30. The XRPD patterns were collected before and after the DVS test and depicted in FIG. 31. Weight gain of Form CSVII under 80% RH is 0.04%. Form CSVII is non hygroscopic or almost non-hygroscopic.

Example 24 Adhesiveness of Form CSVII 30 mg of Form CSVII and WO2016038500 Form 1 were weighed and then added into the dies of φ8 mm round tooling, compressed at 10 KN and held for 30 s. The punch was weighed and amount of material sticking to the punch was calculated. The compression was repeated twice and the cumulative amount, maximum amount and average amount of material sticking to the punch during the compression were recorded. Detailed experimental results are shown in Table 30.

TABLE 30

| Solid form | Average amount (mg) |
|---|---|
| WO2016038500 Form 1 | 0.265 |
| Form CSVII | 0.200 |

Test results indicate that the adhesiveness of Form CSVII is superior to that of the prior art form.

Example 25 Dissolution Profile of Form CSVII Drug Product

Figure 32:
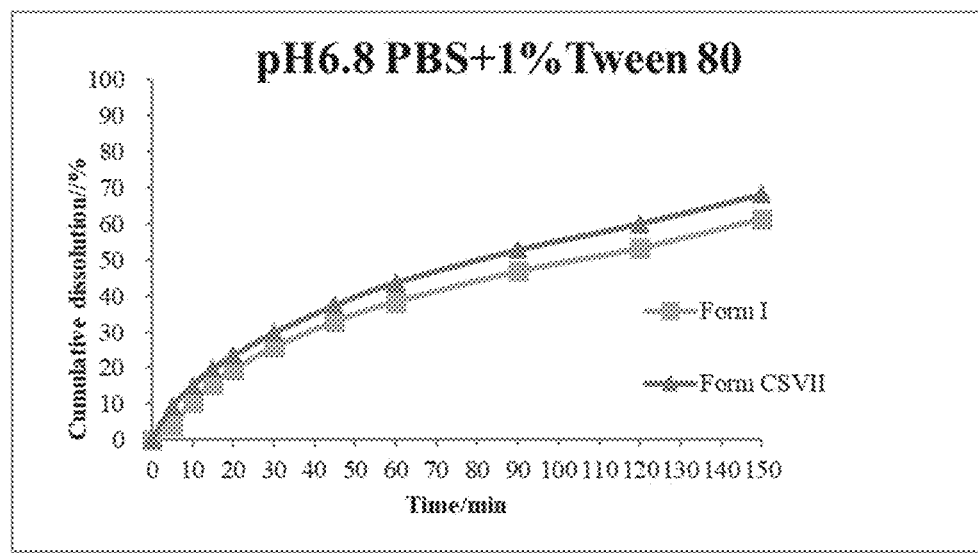
FIG. 32 shows a dissolution curve of Form CSVII drug product and WO2016038500 Form 1 drug product in pH6.8 PBS+1% Tween 80.

Form CSVII and WO2016038500 Form 1 were made into tablets according to formulation and preparation method in Table 31. The cumulative dissolution was measured at different time in pH6.8 PBS+1% Tween 80. The dissolution conditions are listed in Table 32. The dissolution results are presented in Table 33 and FIG. 32.

TABLE 31

| | | Form CSVII | | WO2016038500 Form 1 | | |
|---|---|---|---|---|---|---|
| No. | Component | mg/unit | % (w/w) | mg/unit | % (w/w) | Function |
| | | Intra-granular | | | | |
| 1 | Crystalline API | 75.5 | 37.750 | 61.00 | 30.500 | API |
| 2 | Microcrystalline cellulose | 121.0 | 60.500 | 135.50 | 67.750 | Diluent |
| 3 | Crosslinked povidone | 2.0 | 1.000 | 2.0 | 1.000 | Disintegrant |
| 4 | Magnesium stearate | 0.25 | 0.125 | 0.25 | 0.125 | Lubricant |
| | | Extra-granular | | | | |
| 5 | Crosslinked povidone | 1.0 | 0.500 | 1.0 | 0.500 | Disintegrant |
| 6 | Magnesium stearate | 0.25 | 0.125 | 0.25 | 0.125 | Lubricant |
| | Total | 200.0 | 100.000 | 200.0 | 100.000 | / |

Note:
75.5 mg of Form CSVII is equivalent to 61 mg of Compound I.

TABLE 32

| Equipment | Sotax AT7 |
|---|---|
| Method | Paddle |
| Dose | 61 mg |
| Volume | 900 mL |
| Speed | 75 rpm |
| Temperature | 37° C. |
| Sampling point | pH6.8 PBS + 1% Tween 80: 5, 10, 15, 20, 30, 45, 60, 90, 120, 150 min |
| Media replenishment | No |

TABLE 33

| Time (min) | Cumulative drug release (%) | |
|---|---|---|
| | WO2016038500 Form 1 | Form CSVII |
| 0 | 0.0 | 0.0 |
| 5 | 4.0 | 9.3 |
| 10 | 10.4 | 15.2 |
| 15 | 15.6 | 19.7 |
| 20 | 19.5 | 23.5 |
| 30 | 25.7 | 29.8 |

TABLE 33-continued

| Time | Cumulative drug release (%) | |
|---|---|---|
| (min) | WO2016038500 Form 1 | Form CSVII |
| 45 | 33.0 | 37.4 |
| 60 | 38.4 | 43.7 |
| 90 | 46.8 | 52.8 |
| 120 | 53.3 | 60.1 |
| 150 | 61.4 | 68.3 |

Form CSVII shows higher cumulative drug release than that of WO2016038500 Form 1 in pH6.8 PBS+1% Tween 80. Compared with WO2016038500 Form 1, Form CSVII has better bioavailability.

Comparative Example 1 Stability of Crystalline Form of Compound I in WO2019175263 in Drug Product The crystalline form of Compound I in WO2019175263 was made into drug products according to the formulation and preparation process in Table 34 and Table 35. The XRPD patterns were collected before and after the formulation process. The result shows that the crystalline form of Compound I in WO2019175263 is unstable in the formulation process. Form change occurred during stirring at room temperature.

TABLE 34

| No. | Component | mg/unit | % (w/w) | Function |
|---|---|---|---|---|
| 1 | Crystalline Form of Compound I in WO2019175263 | 61.0 | 10.20 | API |
| 2 | PEG 400 | 398.7 | 66.50 | Diluent |
| 3 | Povidone (PVP K30) | 40.0 | 6.70 | Suspending agent |
| 4 | Polysorbate (Tween 80) | 100.0 | 16.70 | Surfactant |
| 5 | Dibutyl hydroxytoluene | 0.3 | 0.05 | Antioxidant |
|  | Total | 600.0 | 100.00 | / |

TABLE 35

| Stage | Procedure |
|---|---|
| Inner fill preparation | Components No. 2-5 according to formulation were weighed into a glass vial and mixed uniformly. A certain amount of component No.1 according to formulation was added into the previous suspension and then mixed uniformly at room temperature. |

The examples described above are only for illustrating the technical concepts and features of the present disclosure and intended to make those skilled in the art being able to understand the present disclosure and thereby implement it and should not be concluded to limit the protective scope of this disclosure. Any equivalent variations or modifications according to the spirit of the present disclosure should be covered by the protective scope of the present disclosure.

We claim:

1. A crystalline form CSV of tafamidis, wherein the crystalline form CSV is a co-crystal of tafamidis and fumaric acid.

2. The crystalline form CSV according to claim 1, wherein the X-ray powder diffraction pattern comprises characteristic peaks at 2theta values of 13.4°±0.2°, 22.8°±0.2° and 20.8°±0.2° using CuKα radiation.

3. The crystalline form CSV according to claim 1, wherein the X-ray powder diffraction pattern comprises one or two or three characteristic peaks at 2theta values of 18.0°±0.2°, 16.5°±0.2° and 9.6°±0.2° using CuKα radiation.

4. The crystalline form CSV according to claim 1, wherein the X-ray powder diffraction pattern comprises one or two or three characteristic peaks at 2theta values of 15.6°±0.2°, 19.2°±0.2° and 23.9°±0.2° using CuKα radiation.

5. The crystalline form CSV according to claim 1, wherein crystalline form CSV is an anhydrate.

6. A process for preparing crystalline form CSV according to claim 1, wherein the process comprises: adding tafamidis and fumaric acid into a ketone, an ester, an ether, or a mixture of an alcohol and an ether, stirring to obtain crystalline form CSV.

7. A crystalline form CSVI of tafamidis, wherein crystalline form CSVI is a co-crystal of tafamidis and glutaric acid.

8. The crystalline form CSVI according to claim 7, wherein the X-ray powder diffraction pattern comprises characteristic peaks at 2theta values of 14.1°±0.2°, 19.1°±0.2° and 17.2°±0.2° using CuKα radiation.

9. The crystalline form CSVI according to claim 7, wherein the X-ray powder diffraction pattern comprises one or two or three characteristic peaks at 2theta values of 10.0°±0.2°, 22.5°±0.2° and 24.3°±0.2° using CuKα radiation.

10. The crystalline form CSVI according to claim 7, wherein the X-ray powder diffraction pattern comprises one or two or three or four characteristic peaks at 2theta values of 34.1°±0.2°, 33.4°±0.2°, 11.2°±0.2° and 35.5°±0.2° using CuKα radiation.

11. A process for preparing crystalline form CSVI according to claim 7, wherein the process comprises: adding tafamidis and glutaric acid into an ester, stirring to obtain crystalline form CSVI.

12. A crystalline form CSVII of tafamidis, wherein the crystalline form CSVII is a co-crystal of tafamidis and adipic acid.

13. The crystalline form CSVII according to claim 12, wherein the X-ray powder diffraction pattern comprises characteristic peaks at 2theta values of 13.9°±0.2°, 18.8°±0.2° and 25.6°±0.2° using CuKα radiation.

14. The crystalline form CSVII according to claim 12, wherein the X-ray powder diffraction pattern comprises one or two or three characteristic peaks at 2theta values of 24.1°±0.2°, 11.3°±0.2°, and 22.7°±0.2° using CuKα radiation.

15. The crystalline form CSVII according to claim 12, wherein the X-ray powder diffraction pattern comprises one or two or three characteristic peaks at 2theta values of 17.2°±0.2°, 9.8°±0.2°, and 17.0°±0.2° using CuKα radiation.

16. A process for preparing crystalline form CSVII according to claim 12, wherein the process comprises: adding tafamidis and adipic acid into an ester, stirring to obtain crystalline form CSVII.

17. A pharmaceutical composition, wherein the pharmaceutical composition comprises a therapeutically effective amount of crystalline form CSV according to claim 1.

18. A pharmaceutical composition, wherein the pharmaceutical composition comprises a therapeutically effective amount of crystalline form CSVII according to claim 12.

19. A method for treating transthyretin familial amyloid polyneuropathy and/or transthyretin amyloid cardiomyopathy, comprising administering to a subject in need thereof a therapeutically effective amount of crystalline form CSV according to claim 1.

* * * * *